US008551188B2

(12) United States Patent
Lalleman et al.

(10) Patent No.: US 8,551,188 B2
(45) Date of Patent: Oct. 8, 2013

(54) COMPOSITION COMPRISING A HYDROPHOBIC DYE, A PARTICULAR ORGANIC AND/OR MINERAL ALKALINE AGENT, A PARTICULAR COMPOUND (I) AND A PARTICULAR ORGANIC COMPOUND (II), AND DYEING USE THEREOF

(75) Inventors: Boris Lalleman, Paris (FR); Alain Lagrance, Coupvray (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/393,477

(22) PCT Filed: Sep. 1, 2010

(86) PCT No.: PCT/FR2010/051821
§ 371 (c)(1),
(2), (4) Date: May 3, 2012

(87) PCT Pub. No.: WO2011/027077
PCT Pub. Date: Mar. 10, 2011

(65) Prior Publication Data
US 2012/0204357 A1    Aug. 16, 2012

Related U.S. Application Data

(60) Provisional application No. 61/242,130, filed on Sep. 14, 2009, provisional application No. 61/242,437, filed on Sep. 15, 2009, provisional application No. 61/242,440, filed on Sep. 15, 2009, provisional application No. 61/297,439, filed on Jan. 22, 2010.

(30) Foreign Application Priority Data

Sep. 2, 2009   (FR) ..................... 09 55979
Sep. 2, 2009   (FR) ..................... 09 55980
Sep. 2, 2009   (FR) ..................... 09 55982
Dec. 18, 2009  (FR) ..................... 09 59226

(51) Int. Cl.
*A61Q 5/10*    (2006.01)

(52) U.S. Cl.
USPC ............... 8/405; 8/406; 8/435; 8/456; 8/608; 8/611; 8/616; 8/653

(58) Field of Classification Search
USPC ............ 8/405, 406, 435, 456, 608, 611, 616, 8/653
See application file for complete search history.

(56) References Cited

U.S. PATENT DOCUMENTS

| | | |
|---|---|---|
| 3,869,454 A | 3/1975 | Lang et al. |
| 3,955,918 A | 5/1976 | Lang |
| 3,985,499 A | 10/1976 | Lang et al. |
| 4,025,301 A | 5/1977 | Lang |
| 4,151,162 A | 4/1979 | Bugaut et al. |
| 4,153,065 A | 5/1979 | Lang |
| 4,950,306 A | 8/1990 | Marte et al. |
| 5,061,289 A | 10/1991 | Clausen et al. |
| 5,380,340 A | 1/1995 | Neunhoeffer et al. |
| 5,708,151 A | 1/1998 | Moeckli |
| 5,766,576 A | 6/1998 | Loewe et al. |
| 6,099,592 A | 8/2000 | Vidal et al. |
| 6,338,741 B1 | 1/2002 | Vidal et al. |
| 6,406,685 B1 | 6/2002 | Philippe et al. |
| 6,645,258 B2 | 11/2003 | Vidal et al. |
| 6,730,789 B1 | 5/2004 | Birault et al. |
| 7,311,736 B2 | 12/2007 | Burgaud et al. |
| 7,364,596 B2 | 4/2008 | De Boni et al. |
| 7,399,320 B2 | 7/2008 | Burgaud et al. |
| 7,429,275 B2 | 9/2008 | Hercouet et al. |
| 2005/0217038 A1* | 10/2005 | Glenn et al. ............... 8/405 |
| 2007/0180630 A1 | 8/2007 | Javet et al. |
| 2008/0229520 A1 | 9/2008 | Javet et al. |

FOREIGN PATENT DOCUMENTS

| | | |
|---|---|---|
| DE | 2359399 | 6/1975 |
| DE | 3843892 | 6/1990 |
| DE | 4133957 | 4/1993 |
| DE | 4434494 | 3/1996 |
| DE | 19543988 | 5/1997 |
| DE | 102004014763 | 10/2005 |

(Continued)

OTHER PUBLICATIONS

STIC Search Report dated Jun. 25, 2012.*
William M. Meylan and Philip H. Howard, "Atom/Fragment Contribution Method for Estimating Octanol-Water Partition Coefficients," Journal of Pharmaceutical Sciences, vol. 84, No. 1: pp. 83-92, 1995.
Walter Noll, "Chemistry and Technology of Silicones," Academic Press, New York, San Francisco, London, pp. 1-23, 1968.
Search Report for PCT/FR2010/051821, Apr. 13, 2011 (6 pages).
Search Report for FR 0955979, Apr. 27, 2010 (4 pages).
Search Report for FR 0955980, Apr. 29, 2010 (3 pages).
Search Report for FR 0955982, Apr. 27, 2010 (3 pages).
Search Report for FR 0959226, Sep. 27, 2010 (2 pages).
English language abstract of DE 102004052480.
English language abstract of DE 4434494, (1996).
English language abstract of EP 0770375, (1997).
English language abstract of FR 2886136, ((2006).
English language abstract of FR 2889946, (2007).
English language abstract of JP 2-19576, (1990).
English language abstract of JP 05-163124, (1993).

*Primary Examiner* — Eisa Elhilo
(74) *Attorney, Agent, or Firm* — O'Brien Jones, PLLC

(57) ABSTRACT

Composition comprising a hydrophobic dye, a particular organic and/or mineral alkaline agent, a particular compound (I) and a particular organic compound (II), and dyeing use thereof. The present invention relates to a dye composition comprising one or more hydrophobic direct dyes with a log P of greater than or equal to 2, one or more organic alkaline agents, and/or one or more mineral alkaline agents chosen from carbonates, hydrogen carbonates, sodium hydroxide and potassium hydroxide, and mixtures thereof, one or more compounds (I) comprising in their structure a sequence:

$$\overset{\text{O}}{\underset{\|}{\text{C}}}-(CH_2)_n-X$$

and
one or more organic compounds (II) with a Hansen solubility parameter δH of less than or equal to 16 MPa$^{1/2}$ and with a molecular weight of less than 250 g/mol. The invention also relates to a dyeing process that consists in applying such a composition to keratin fibers.

14 Claims, No Drawings

(56) References Cited

FOREIGN PATENT DOCUMENTS

| | | |
|---|---|---|
| DE | 102004014764 | 10/2005 |
| DE | 102004052480 | 5/2006 |
| DE | 102007042286 | 3/2009 |
| EP | 0173109 | 3/1986 |
| EP | 0357548 | 3/1990 |
| EP | 0714954 | 6/1996 |
| EP | 0770375 | 5/1997 |
| EP | 1378544 | 1/2004 |
| EP | 1627626 | 6/2006 |
| EP | 1674073 | 6/2006 |
| FR | 2140205 | 1/1973 |
| FR | 2189006 | 1/1974 |
| FR | 2285851 | 4/1976 |
| FR | 2733749 | 11/1996 |
| FR | 2771286 | 5/1999 |
| FR | 2801308 | 5/2001 |
| FR | 2886136 | 12/2006 |
| FR | 2889946 | 3/2007 |
| GB | 1026978 | 4/1966 |
| GB | 1153196 | 5/1969 |
| JP | 2-19576 | 1/1990 |
| JP | 5-163124 | 6/1993 |
| WO | 94/08969 | 4/1994 |
| WO | 94/08970 | 4/1994 |
| WO | 95/01772 | 1/1995 |
| WO | 95/15144 | 6/1995 |
| WO | 96/15765 | 5/1996 |
| WO | 2009/033833 | 3/2009 |

* cited by examiner

COMPOSITION COMPRISING A HYDROPHOBIC DYE, A PARTICULAR ORGANIC AND/OR MINERAL ALKALINE AGENT, A PARTICULAR COMPOUND (I) AND A PARTICULAR ORGANIC COMPOUND (II), AND DYEING USE THEREOF

CROSS REFERENCE TO RELATED APPLICATIONS

This is a national stage application of PCT/FR2010/051821, filed internationally on Sep. 1, 2010, which claims priority to U.S. Provisional Application No. 61/242,130, filed on Sep. 14, 2009, U.S. Provisional Application No. 61/242,437, filed on Sep. 15, 2009, U.S. Provisional Application No. 61/242,440, filed on Sep. 15, 2009, and U.S. Provisional Application No. 61/297,439, filed on Jan. 22, 2010, as well as French Application No. 0955979, filed on Sep. 2, 2009, French Application No. 0955980, filed on Sep. 2, 2009, French Application No. 0955982, filed on Sep. 2, 2009, and French Application No. 0959226, filed on Dec. 18, 2009, all of which are incorporated herein by reference in their entireties.

BACKGROUND OF THE INVENTION

1. Field of the Invention

The present invention relates to a composition for dyeing human keratin fibers, comprising at least one hydrophobic dye, at least one organic alkaline agent and/or at least one particular mineral base, at least one particular compound (I) and at least one particular organic compound (II), and also to a dyeing process.

2. Description of the Relevant Art

Two major methods for dyeing human keratin fibers, and in particular the hair, are known.

The first, known as oxidation dyeing or permanent dyeing, consists in using one or more oxidation dye precursors, more particularly one or more oxidation bases optionally combined with one or more couplers.

Oxidation bases are usually selected from ortho- or para-phenylenediamines, ortho- or para-aminophenols, and heterocyclic compounds. These oxidation bases are colorless or weakly colored compounds, which, when combined with oxidizing products, can give rise via a process of oxidative condensation to colored species, which remain trapped within the fiber.

The shades obtained with these oxidation bases are often varied by combining them with one or more couplers, these couplers being chosen especially from aromatic meta-diamines, meta-aminophenols, meta-diphenols and certain heterocyclic compounds, such as indole compounds.

The variety of molecules used as oxidation bases and couplers allows a wide range of colors to be obtained.

Oxidation dyeing processes are generally performed by applying to keratin fibers oxidation dye precursors (one or more oxidation bases, optionally combined with one or more couplers) in the presence of an oxidizing agent, especially such as hydrogen peroxide (or aqueous hydrogen peroxide solution), which is mixed with the dye composition just before its use.

The resulting colorations are generally powerful and show good fastness especially with respect to shampooing.

However, the conditions of use are liable to lead to degradation of keratin fibers. In the long run, these fibers are more or less degraded and have a tendency to become coarse, dull, brittle and difficult to style, especially in the case of repeated dyeing.

The second dyeing method, known as direct dyeing or semi-permanent dyeing, comprises the application of direct dyes, which are molecules with affinity for the fibers and which color even in the absence of an oxidizing agent added to the compositions containing them. Given the nature of the molecules used, they tend rather to remain on the surface of the fiber and penetrate relatively little into the fiber, when compared with the small molecules of oxidation dye precursors.

The direct dyes generally used are chosen from nitrobenzene, anthraquinone, nitropyridine, azo, methine, azomethine, xanthene, acridine, azine and triarylmethane direct dyes. The chemical species used may be nonionic, anionic (acidic dyes) or cationic (basic dyes). Direct dyes may also be natural dyes.

The majority of the direct dyes used have sufficient solubility in aqueous medium, and numerous dye supports suitable for using them now exist.

These compositions containing one or more direct dyes are applied to keratin fibers for a time necessary to obtain the desired coloration, and are then rinsed out.

However, the colorations resulting therefrom are particularly chromatic colorations, but are, however, only temporary or semi-permanent since the nature of the interactions that bind the direct dyes to the keratin fiber and their desorption from the surface and/or the core of the fiber are responsible for their weak dyeing power and their poor fastness with respect to washing or to light.

Thus, the known processes for dyeing the hair, whether in the field of direct dyeing or oxidation dyeing, have room for improvement.

In particular, there is a need to provide processes for dyeing human keratin fibers that can respect the nature of these fibers and that in particular avoid their degradation, while at the same time affording powerful dyeing results, and being resistant to external agents, in particular to washing, perspiration, light, UV radiation, bad weather, rubbing and chemical treatments, such as permanent-waving treatments.

This need is in particular felt in the case of blue dyes, whose fastness with respect to light and to UV radiation is generally unsatisfactory.

To efficiently color keratin fibers, the majority of hydrophobic direct dyes must be used in the presence of particular solvents, whose role is to convey them into the fiber. Among the cosmetic solvents known for this purpose, aromatic solvents are frequently used. Mention may be made more particularly of benzyl alcohol, benzyloxyethanol or phenoxyethanol.

However, the presence of the aromatic solvents, which are sparingly soluble in aqueous medium, makes it necessary to use large amounts of cosolvents, usually ethanol, in order to make them compatible with standard dye formulations.

Moreover, even under these conditions, the intensity of the colorations obtained remains insufficient or the selectivity remains too high.

In addition, reducing agents such as hydrosulfites are occasionally used in the textile field, in order to reduce reducible hydrophobic dyes. However, these compounds are harmful to the environment, and especially contaminate the waste water extensively. Moreover, they give off very unpleasant odors, which make them unsuitable for use in the cosmetics field.

There is thus a need to provide novel compositions based on hydrophobic dyes for dyeing human hair, which are more efficient, while at the same time being compatible with hydrophobic dyes, and which respect both the environment and the nature of the hair. These compositions must also make it possible to obtain powerful, unselective and resistant dyeing results.

Patent application FR 2 771 286 in the name of the Applicant describes, in general, the use of compounds of indigoid type in cosmetic compositions, and more particularly in makeup compositions such as lipsticks, foundations, face powders, eyeshadows, loose or compact powders, eyeliners, mascaras and nail varnishes.

DETAILED DESCRIPTION OF THE PREFERRED EMBODIMENTS

The Applicant has discovered, surprisingly, that the problems outlined above can be solved with a dye composition comprising one or more hydrophobic direct dyes with a log P of greater than or equal to 2, one or more organic alkaline agents and/or one or more particular mineral bases, one or more particular compounds (I) and one or more particular organic compounds (II).

One subject of the invention is thus a dye composition comprising:

one or more hydrophobic direct dyes with a log P of greater than or equal to 2,
one or more organic alkaline agents, and/or one or more mineral bases chosen from carbonates, hydrogen carbonates, sodium hydroxide and potassium hydroxide, and mixtures thereof,
one or more compounds (I) comprising in their structure a sequence:

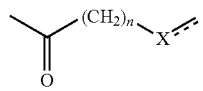

with n denoting an integer ranging from 0 to 4, and

denoting a group:

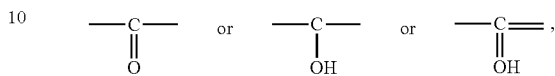

and
one or more organic compounds (II) with a Hansen solubility parameter $\delta H$ of less than or equal to 16 $MPa^{1/2}$ and with a molecular weight of less than 250 g/mol.

The log P value conventionally represents the partition coefficient of the dye between octanol and water. The log P may be calculated according to the method described in the article by Meylan and Howard *Atom/fragment contribution method for estimating octanol-water partition coefficient*, J. Pharm. Sci. 84, 83-92 (1995). This value may also be calculated by means of numerous software packages available on the market, which determine the log P as a function of the structure of a molecule. An example that may be mentioned is the Epiwin software from the United States Environmental Agency.

It should be noted that the log P value is usually given for a temperature of 25° C. and at atmospheric pressure (760 mmHg, i.e. $1.013 \times 10^5$ Pa).

In particular, the hydrophobic direct dye(s) present in the composition according to the invention may be chosen especially from the following compounds, alone or as a mixture:

| Dye | Chemical structure | logP |
|---|---|---|
| Disperse Red 17 | 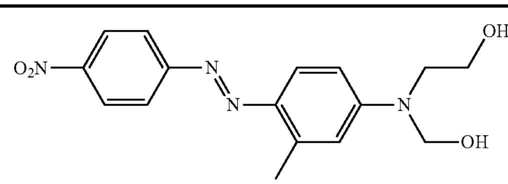 | 3.69 |
| Disperse Violet 1 | 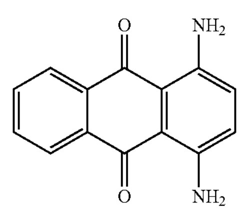 [SMILES: Nc1ccc(N)c2c1C(=O)c1ccccc1C2=O] | 3.0 |
| HC Yellow 7 | 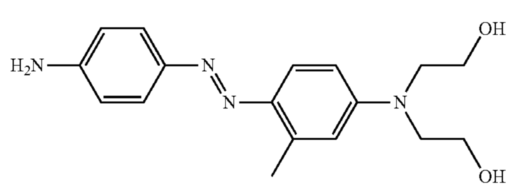 [SMILES: Cc1cc(N(CCO)CCO)ccc1/N=N/c1ccc(N)cc1] | 2.38 |

-continued

| Dye | Chemical structure | logP |
|---|---|---|
| Disperse Blue 377 | 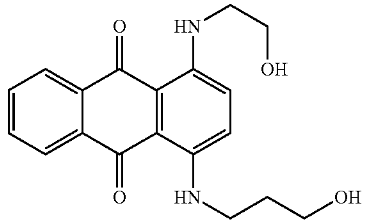 [SMILES: O=C1c2ccccc2C(=O)c2c(NCCCO)ccc(NCCO)c21] | 3.21 |
| Disperse Red 13 | 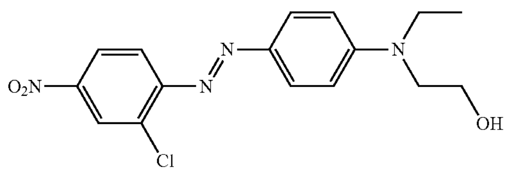 [SMILES: CCN(CCO)c1ccc(/N=N/c2ccc([N+](=O)[O-])cc2Cl)cc1] | 5.22 |
| Disperse Green 9 | 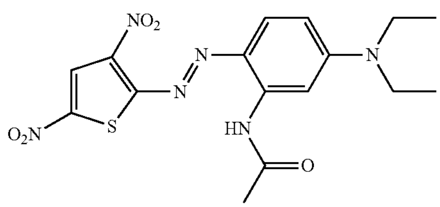 [SMILES: CCN(CC)c1ccc(/N=N/c2sc([N+](=O)[O-])cc2[N+](=O)[O-])c(NC(C)=O)c1] | 4.23 |
| Solvent Black 3 | 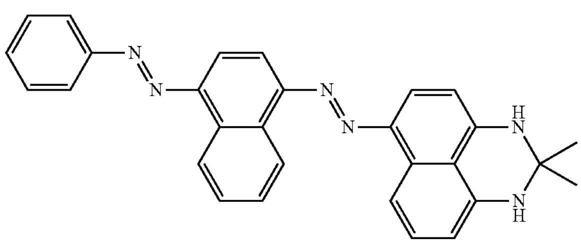 [SMILES: CC1(C)Nc2cccc3c(/N=N/c4ccc(/N=N/c5ccccc5)c5ccccc45)ccc(c23)N1] | 7.50 |
| Disperse Blue 148 | 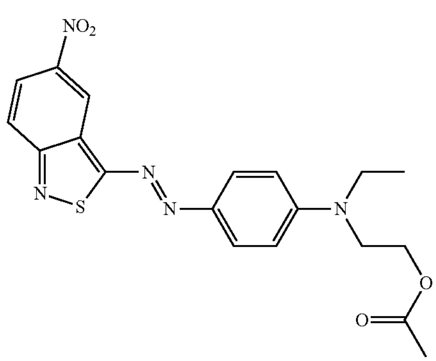 [SMILES: CCN(CCOC(C)=O)c1ccc(/N=N/c2snc3ccc([N+](=O)[O-])cc23)cc1] | 4.81 |
| Disperse Violet 63 | 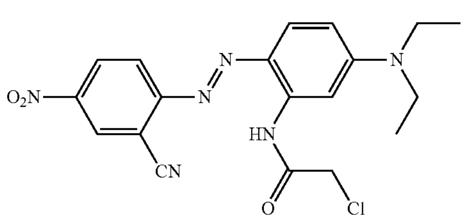 [SMILES: CCN(CC)c1ccc(/N=N/c2ccc([N+](=O)[O-])cc2C#N)c(NC(=O)CCl)c1] | 5.30 |

-continued
| Dye | Chemical structure | logP |
|---|---|---|
| Disperse Blue 60 | 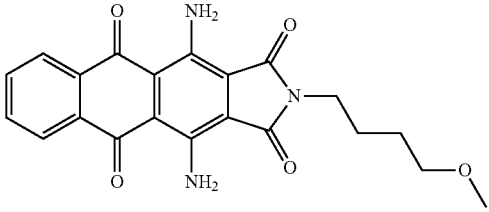 [SMILES: COCCCCn1c(=O)c2c(N)c3c(=O)c4ccccc4c(=O)c3c(N)c2c1=O] | 3.38 |
| Disperse Blue 14 | 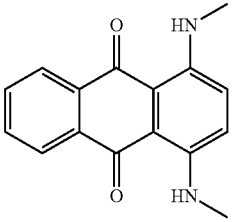 [SMILES: CNc1ccc(NC)c2c1C(=O)c1ccccc1C2=O] | 4.25 |
| Solvent Orange 15 | 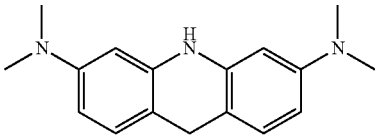 | 3.90 |
| Solvent Orange 7 | 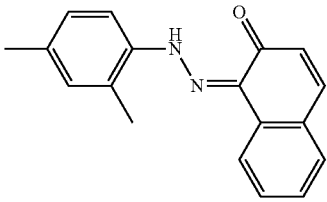 [SMILES: Cc1ccc(N/N=C2\C(=O)C=Cc3ccccc32)c(C)c1] | 4.40 |
| Solvent Blue 14 | 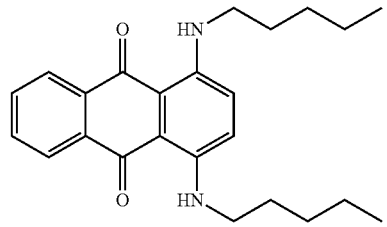 [SMILES: CCCCCNc1ccc(NCCCCC)c2c1C(=O)c1ccccc1C2=O] | 8.18 |
| Disperse Yellow 82 | 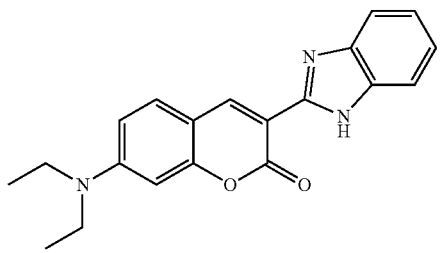 [SMILES: CCN(CC)c1ccc2cc(-c3nc4ccccc4[nH]3)c(=O)oc2c1] | 3.68 |

The hydrophobic direct dye(s) present in the composition according to the invention may also be chosen from indigoid dyes.

The indigoid dyes that may be used in the composition according to the invention may be chosen from:

| Name | Dye principles |
|---|---|
| Indigo | 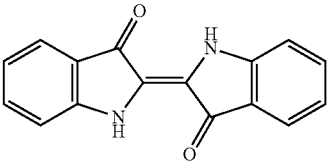 [SMILES: O=C1/C(=C2\Nc3ccccc3C2=O)Nc2ccccc21] |
| Isoindigo | 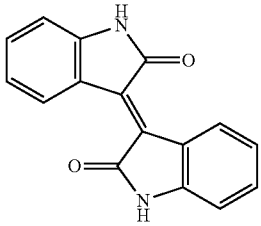 [SMILES: O=C1Nc2ccccc2/C1=C1\C(=O)Nc2ccccc21] |
| Indirubin | 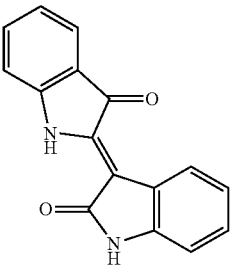 [SMILES: O=C1Nc2ccccc2/C1=C1/Nc2ccccc2C1=O] |
| Isoindirubin | 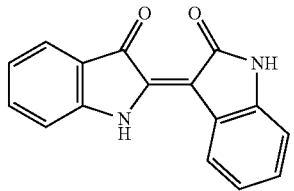 [SMILES: O=C1Nc2ccccc2/C1=C1\Nc2ccccc2C1=O] |
| 4,4'-dibromoindigo | 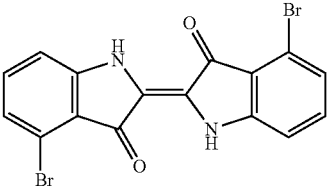 [SMILES: O=C1/C(=C2\Nc3cccc(Br)c3C2=O)Nc2cccc(Br)c21] |
| 6,6'-dibromoindigo | 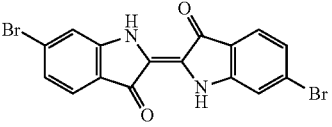 [SMILES: O=C1/C(=C2\Nc3cc(Br)ccc3C2=O)Nc2cc(Br)ccc21] |
| 5,5'-dibromoindigo | 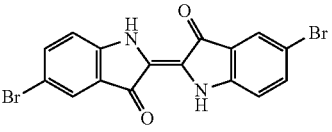 [SMILES: O=C1/C(=C2\Nc3ccc(Br)cc3C2=O)Nc2ccc(Br)cc21] |
| cis-6,6'-dibromoindigo | 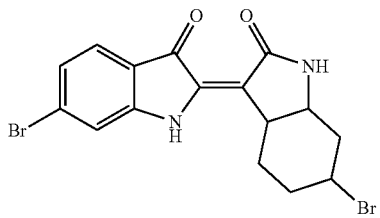 [SMILES: O=C1NC2CC(Br)CCC2/C1=C1\Nc2cc(Br)ccc2C1=O] |
| 5,5',7,7'-tetrabromoindigo | 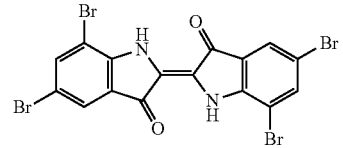 [SMILES: O=C1/C(=C2\Nc3c(Br)cc(Br)cc3C2=O)Nc2c(Br)cc(Br)cc21] |
| 4,4',7,7'-tetrachloroindigo | 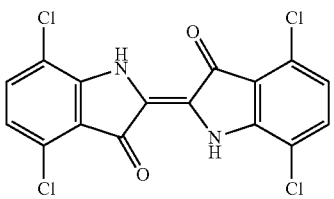 [SMILES: O=C1/C(=C2\Nc3c(Cl)ccc(Cl)c3C2=O)Nc2c(Cl)ccc(Cl)c21] |
| 3H-Indol-3-one, 1,2-dihydro-2-(3-oxobenzo[b]thien-2(3H)-ylidene) | 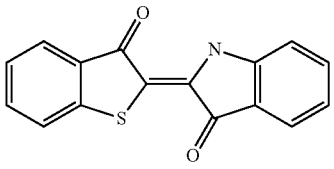 [SMILES: O=C1/C(=C2\Sc3ccccc3C2=O)Sc2ccccc21] |
| Thioindigo (other names: C.I. 73300 C.I. Disperse Red 364 C.I. Solvent Red 242 C.I. Vat Red 41 Ciba Pink B Disperse Red 364) | 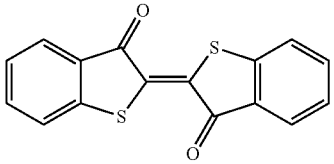 |
| Vat Red 1 (Oralith) | 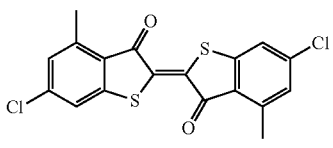 [SMILES: Cc1cc(Cl)cc2c1C(=O)/C(=C1\Sc3cc(Cl)cc(C)c3C1=O)S2] |
| Cis-Thioindigo (Benzo[b]thiophen-3(2H)-one, 2-(3-oxobenzo[b]thien-2(3H)-ylidene)-, (2Z)) | 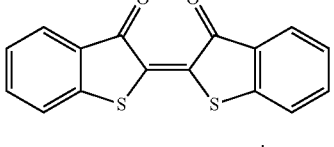 |
| 6,6'-dichloro-4,4'-dimethylindigo | 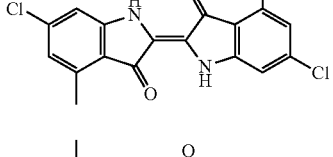 |
| 5,5'-dichloro-7,7'-dimethylindigo | 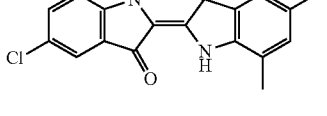 |

| Name | Dye principles |
|---|---|
| 4,4',7,7'-tetramethylindigo | 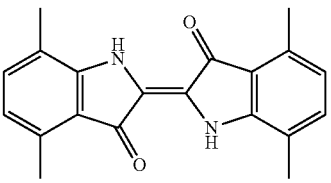 [SMILES: Cc1ccc(C)c2c1N/C(=C1/Nc3c(C)ccc(C)c3C1=O)C2=O] |
| Thioindigo Scarlet R (other names: 2H-Indol-2-one, 1,3-dihydro-3-(3-oxobenzo[b]thien-2(3H)-ylidene; C.I. 73635) | 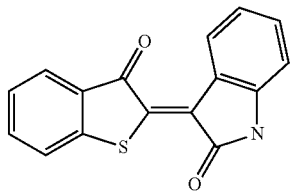 [SMILES: O=C1Nc2ccccc2/C1=C1/Sc2ccccc2C1=O] |
| 2H-Indol-2-one, 1,3-dihydro-3-(3-oxobenzo[b]thien-2(3H)-ylidene)-, (3E)- | 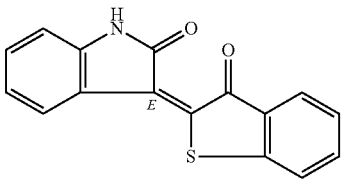 [SMILES: O=C1Nc2ccccc2/C1=C1\Sc2ccccc2C1=O] |
| Thioindirubin (Benzo[b]thiophen-3(2H)-one, 2-(2-oxobenzo[b]thiophen-3(2H)-ylidene)) | 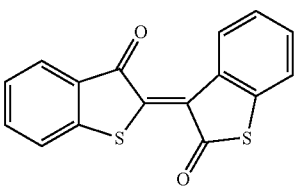 [SMILES: O=C1Sc2ccccc2/C1=C1/Sc2ccccc2C1=O] |
| 2H-Indol-2-one, 1,3-dihydro-3-(2-oxobenzo[b]thiophen-3(2H)-ylidene)- | 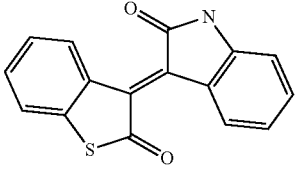 [SMILES: O=C1Nc2ccccc2/C1=C1\C(=O)Sc2ccccc21] |
| Benzo[b]thiophen-2(3H)-one, 3-(2-oxobenzo[b]thiophen-3(2H)-ylidene) | 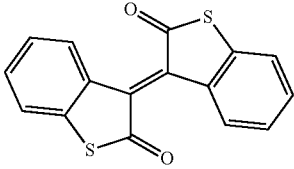 [SMILES: O=C1Sc2ccccc2/C1=C1\C(=O)Sc2ccccc21] |

It is also possible to use, as hydrophobic direct dyes with a log P of greater than or equal to 2, the following indigoid direct dyes: leucoindigo, leucoisoindigo, leucoindirubin, leucoisoindirubin.

The hydrophobic direct dye(s) present in the composition according to the invention may also be chosen from the compounds of formulae (III) and (IV) below:

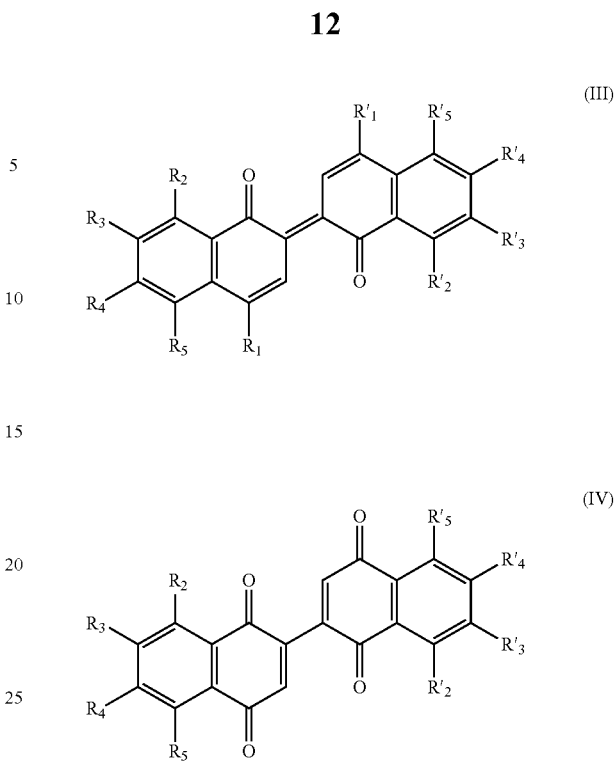

in which:

$R_1$, $R'_1$, $R_2$, $R'_2$, $R_3$, $R'_3$, $R_4$, $R'_4$, $R_5$ and $R'_5$, which may be identical or different, represent a hydrogen atom, a halogen atom, a hydroxyl radical, a $C_1$ to $C_{30}$ alkyl, $C_1$ to $C_{30}$ alkyloxy, $C_1$ to $C_{30}$ acyl or $C_1$ to $C_{30}$ acyloxy radical, the alkyl and alkyloxy radicals possibly being substituted with one or more halogen atoms and/or with one or more hydroxyl groups.

Preferably, the direct dyes with a log P of greater than or equal to 2 are chosen from indigoid dyes and the compounds of formulae (III) and (IV).

In formulae (III) and (IV) above, the term "halogen atom" in particular denotes chlorine, bromine, iodine and fluorine atoms.

Preferably, the radicals $R_1$ and $R'_1$, which may be identical or different, represent a hydrogen atom, a $C_1$ to $C_{10}$ alkyl radical or a $C_1$ to $C_{10}$ alkyloxy radical, these radicals possibly being substituted with one or more halogen atoms and/or with one or more hydroxyl groups.

Particularly preferably, the radicals $R_1$ and $R'_1$, which may be identical or different, represent a hydrogen atom or a $C_1$ to $C_8$ alkyloxy radical.

Preferably, the radicals $R_2$, $R'_2$, $R_3$, $R'_3$, $R_4$, $R'_4$, $R_5$ and $R'_5$, which may be identical or different, represent a hydrogen atom, a halogen atom, a hydroxyl radical or a $C_1$ to $C_{10}$ alkyl or alkyloxy radical, these radicals possibly being substituted with one or more halogen atoms and/or with one or more hydroxyl groups.

Particularly preferably, the radicals $R_2$, $R'_2$, $R_3$, $R'_3$, $R_4$, $R'_4$, $R_5$ and $R'_5$, which may be identical or different, represent a hydrogen atom, a hydroxyl radical, a $C_1$ to $C_8$ alkyl radical or a $C_1$ to $C_8$ alkyloxy radical.

Among the compounds of formula (III) that may be used in the compositions according to the invention, the following compounds are more particularly preferred:

| Name | Structure |
|---|---|
| Indigo Russig's Blue | 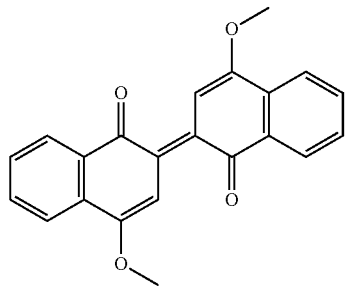 [SMILES: COC1=C/C(=C2/C=C(OC)c3ccccc3C2=O)C(=O)c2ccccc21] |
| Diosindigo A | 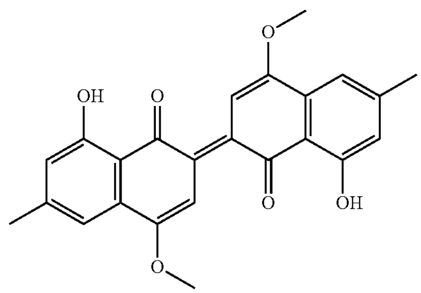 |
| Diosindigo B | 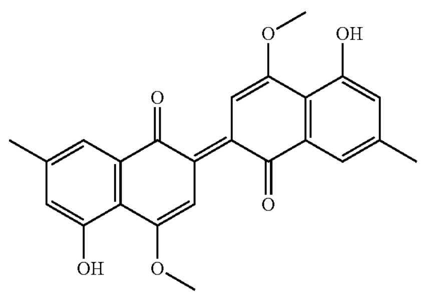 |
| 4,4'-diethoxy-2,2'-binaphthylidene-1,1'-dione | 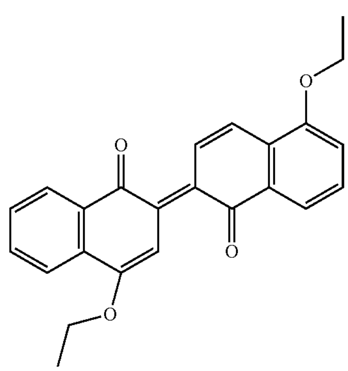 [SMILES: CCOC1=C/C(=C2/C=Cc3c(OCC)cccc3C2=O)C(=O)c2ccccc21] |
| 4,4'-bis(hexyloxy)-1H,14H-2,2'-binaphthalene-1,1'-dione | 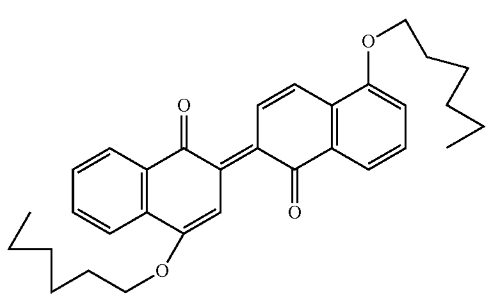 [SMILES: CCCCCCOC1=C/C(=C2/C=Cc3c(OCCCCCC)cccc3C2=O)C(=O)c2ccccc21] |

Among the compounds of formula (II) that may be used in the compositions according to the invention, the following compounds are more particularly preferred:

| Name | Structure |
|---|---|
| mamegakinone | 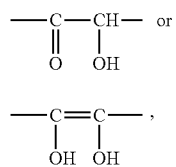 |
| biramentaceone | 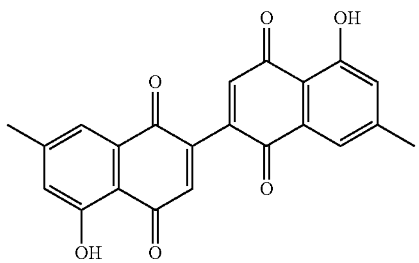 |

The hydrophobic direct dye(s) with a log P of greater than or equal to 2 generally represent from 0.001% to 20% by weight, preferably from 0.01% to 20% by weight, preferentially from 0.01% to 10% by weight, even more preferentially from 0.05% to 10% by weight and better still from 0.1% to 5% by weight relative to the total weight of the cosmetic composition.

As explained previously, the composition according to the invention also comprises one or more particular compounds (I).

Preferably, the integer n denotes 0, 1 or 2.

Preferably, the compounds (I) have in their structure a sequence:

(A)

$$-\underset{\underset{O}{\|}}{C}-\underset{\underset{OH}{|}}{CH}- \quad \text{or}$$

(B)

$$-\underset{\underset{OH}{|}}{C}=\underset{\underset{OH}{|}}{C}-,$$

(B) being the tautomeric form of (A).

Compound(s) (I) more preferentially correspond to formula (C) below:

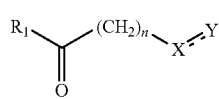

(C)

with:

n denoting an integer from 0 to 4 and preferably from 0 to 2, and

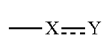

denoting a group:

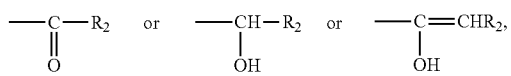

$R_1$ and $R_2$ representing, independently of each other, a hydrogen atom; a substituted or unsubstituted phenyl radical; a hydroxyl radical; a $C_1$-$C_4$ alkoxy radical; a linear or branched $C_1$-$C_4$ alkyl radical, which is unsubstituted or substituted with one or two radicals chosen from the radicals —OR', —C(O)R" and —COOR'", with R', R" and R'" representing, independently of each other, a hydrogen atom or a linear or branched $C_1$-$C_4$ alkyl radical, or $R_1$ and $R_2$ forming, with the carbon-based chain to which they are attached, an unsubstituted 5- or 6-membered nonaromatic carbon-based ring.

The particular compound(s) (I) are preferably chosen from the following compounds:

| | |
|---|---|
| Hydroxyacetone | |
| Acetoin | |
| Glutaroin | |
| Adipoin | |
| Dihydroxyacetone | |
| Glycol aldehyde | |
| Benzoin | |
| 2,3-Dihydroxyacrylaldehyde | |

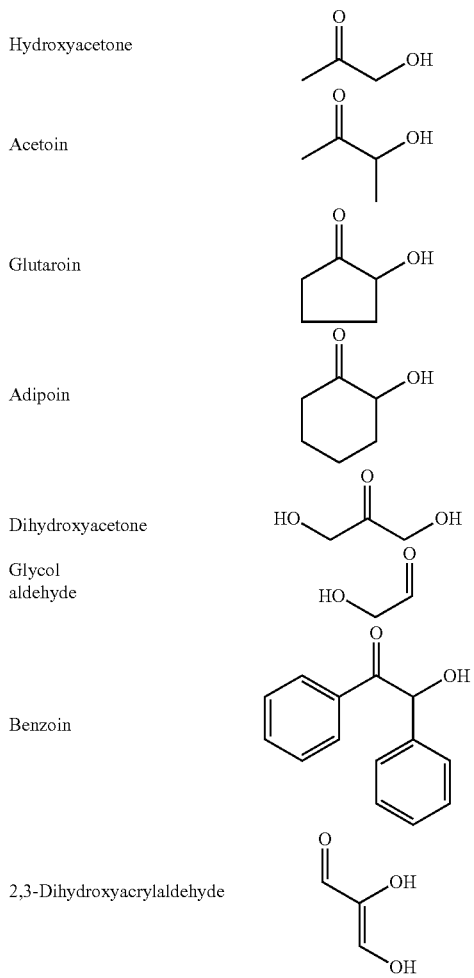

-continued

| | |
|---|---|
| Cyclopentane dione | 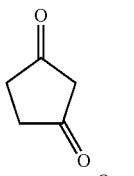 |
| Acetonylacetone | 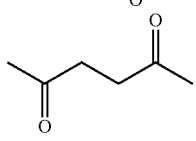 |
| Acetylacetone | 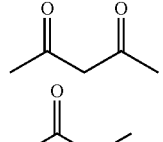 |
| diacetyl | 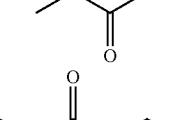 |
| dipropionyl | 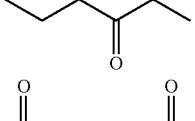 |
| 2-Ketoglutaric acid | 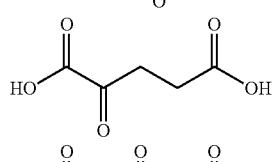 |
| 3-Ketoglutaric acid | 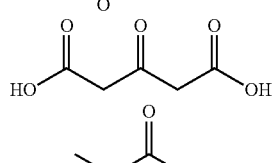 |
| Pyruvic acid | 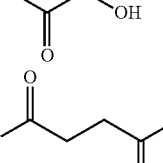 |
| Levulinic acid | 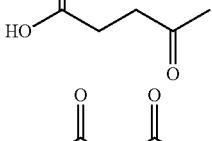 |
| Acetoacetic acid | 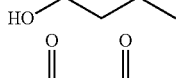 |
| Propionylacetic acid | 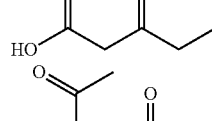 |
| Acetonylmalonic acid | 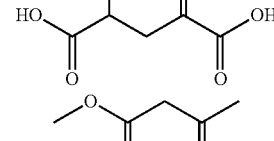 |
| Methyl acetoacetate | 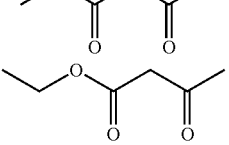 |
| Ethyl acetoacetate | 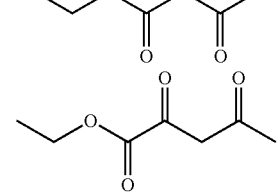 |
| Acetopyruvic acid |  |

-continued

| | |
|---|---|
| Cyclohexanedione | 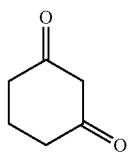 |

The preferred compound(s) (I) are the α-hydroxyacetone compounds, such as hydroxyacetone, acetoin, glutaroin, adipoin, benzoin, dihydroxyacetone, glycol aldehyde and 2,3-dihydroxyacryl aldehyde.

Compound(s) (I) generally represent from 0.01% to 20% by weight, preferably from 0.05% to 10% by weight and better still from 0.1% to 5% by weight relative to the total weight of the cosmetic composition.

The composition according to the invention also comprises one or more organic alkaline agents, and/or one or more mineral bases chosen from carbonates, hydrogen carbonates, sodium hydroxide and potassium hydroxide, and mixtures thereof, and preferably from organic alkaline agents, and/or one or more mineral bases chosen from carbonates and hydrogen carbonates, and mixtures thereof.

For the purposes of the invention, the term "organic alkaline agent" means any organic compound which, via its presence in the composition, increases the pH of the composition by at least 0.05 pH unit and preferably by at least 0.1 pH unit.

Preferably, the organic alkaline agent(s) of the invention have a $pK_b$ at 25° C. ranging from 1 to 12.

As is known per se, for an alkaline agent, the term "$pK_b$" denotes the value corresponding to $-\log(K_b)$, with $K_b$ denoting the dissociation constant in water of this alkaline agent. When the organic alkaline agent comprises more than one basic function, it should be noted that the $pK_b$ according to the invention corresponds to the function of highest basicity.

Preferably, the organic alkaline agent(s) according to the invention have a $pK_b$ at 25° C. ranging from 1 to 10 and more preferentially from 2 to 6.

More preferably, the organic alkaline agent(s) according to the invention are chosen from organic amines with a $pK_b$ at 25° C. as defined above.

Thus, according to a first variant, the organic alkaline agent(s) according to the invention are chosen from amines comprising a primary, secondary or tertiary amine function and one or more linear or branched $C_1$-$C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for use.

Among compounds of this type, mention may be made of monoethanol amine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

According to a second variant, the organic alkaline agent(s) according to the invention are chosen from the organic amines having the following formula:

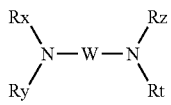

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

According to a third variant, the organic alkaline agent(s) according to the invention are chosen from amino acids.

More particularly, the amino acids that may be used are of natural or synthetic origin, in their L, D or racemic form, and comprise at least one acid function chosen more particularly from carboxylic acid, sulfonic acid, phosphonic acid or phosphoric acid functions. The amino acids may be in neutral or ionic form.

As amino acids that may be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

The preferred amino acids are basic amino acids comprising an additional amine function optionally included in a ring or in a ureido function.

Such basic amino acids are preferably chosen from those corresponding to formula (V) below:

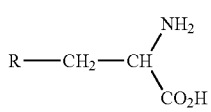

(V)

in which R denotes a group chosen from:

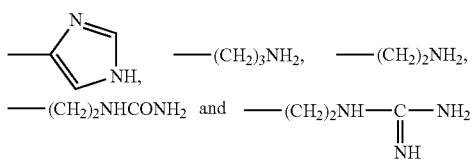

The compounds corresponding to formula (V) are histidine, lysine, arginine, ornithine and citrulline.

According to a fourth variant, the organic alkaline agent(s) according to the invention are chosen from organic amines of heterocyclic type. Besides histidine that has already been mentioned in the amino acids, mention may in particular be made of pyridine, piperidine, imidazole, triazole, tetrazole and benzimidazole.

According to a fifth variant, the organic alkaline agent(s) according to the invention are chosen from amino acid dipeptides. As amino acid dipeptides that may be used in the present invention, mention may be made especially of carnosine, anserine and baleine.

According to a sixth variant, the organic alkaline agent(s) according to the invention are chosen from compounds comprising a guanidine function. Thus, the organic alkaline agent may be chosen from guanidine, arginine that has already been mentioned as an amino acid, creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Preferably, the organic alkaline agent(s) are chosen from alkanolamines, basic amino acids and compounds comprising a guanidine function, and mixtures thereof.

Even more preferably, the organic alkaline agent(s) are chosen from alkanolamines, in particular monoethanolamine, diethanolamine and triethanolamine.

As is known per se, the term "carbonate" denotes a salt containing the anion $CO_3^{2-}$.

As is known per se, the term "hydrogen carbonate", also known as bicarbonate, denotes a salt containing the anion $HCO_3^-$.

Preferably, the mineral base(s) are chosen from alkali metal carbonates and alkali metal hydrogen carbonates, and mixtures thereof.

The preferred alkali metals are lithium, sodium and potassium.

According to one particularly preferred embodiment, the mineral base(s) are chosen from sodium carbonate, potassium carbonate, sodium hydrogen carbonate and potassium hydrogen carbonate, and mixtures thereof.

The organic alkaline agent(s) and/or the mineral base(s) represent from 0.1% to 20% by weight, preferably from 0.5% to 10% by weight and more preferentially from 1% to 5% by weight relative to the total weight of the composition.

The composition according to the invention also comprises one or more organic compounds (II) with a Hansen solubility parameter value δH of less than 16, more preferentially between 5 and 15.8 $MPa^{1/2}$, even more preferentially between 8 and 15.8 $MPa^{1/2}$ and better still between 8 and 15 $MPa^{1/2}$.

Preferably, these compounds are liquid at a temperature of 25° C. and at atmospheric pressure (760 mmHg; i.e. $1.013 \times 10^5$ Pa).

The organic compound(s) having a Hansen solubility parameter value δH as defined previously are, for example, described in the reference publication *Hansen solubility parameters: A User's Handbook* by Charles M. Hansen, CRC Press, 2000, pages 167 to 185, or in the publication *Handbook of Solubility Parameters and Other Cohesion Parameters*, CRC Press, pages 95 to 121 and pages 177 to 185.

This solubility parameter value δH is linked to the formation of hydrogen bonds.

In particular, the publication *Handbook of Solubility Parameters and Other Cohesion Parameters*, CRC Press, pages 95 to 121 and pages 177 to 185, gives the equation $\delta H = (\Sigma - {}^z U_h / V)^{1/2}$ where ${}^z U_h$ (in $J \cdot mol^{-1}$) describes the contributions of the functional group considered in the solubility parameters linked to the hydrogen bonds (values in Table 14, page 183); this parameter $^2U_h$ is also described in the publication *The relation between surface tension and solubility parameter in liquids*, Bagda, E, Farbe Lack, 84, 212, 1978;

and V is the volume of the molecule.

It should be noted that the solubility parameter value δH is usually given for a temperature of 25° C. and at atmospheric pressure (760 mmHg, i.e. $1.013 \times 10^5$ Pa).

Said organic compound(s) (II) may be chosen from alkanols, aliphatic esters, ethers, aromatic alcohols, alkylaryl alcohols, aromatic acids, aliphatic acids, alkylene carbonates such as propylene carbonate, and lactones such as γ-butyrolactone, and mixtures thereof.

Preferably, said organic compound(s) (II) are chosen from alkanols, aliphatic esters, ethers, aromatic alcohols, alkylaryl alcohols, aromatic acids and aliphatic acids, and mixtures thereof.

Even more preferentially, said organic compound(s) (II) are chosen from 1-octanol, 1-decanol, tridecyl alcohol, dipropylene glycol monomethyl ether acetate, dipropylene glycol methyl ether, tripropylene glycol methyl ether, propylene glycol n-butyl ether, propylene glycol n-propyl ether, propylene glycol monomethyl ether, diethylene glycol monomethyl ether and monoethyl ether, 3-phenyl-1-propanol, 2-phenyl-1-propanol, benzyl alcohol, benzyloxyethanol and phenoxyethanol, and mixtures of these compounds.

The organic compound (II) is preferably chosen from aromatic alcohols and alkylaryl alcohols and even more preferentially benzyl alcohol.

When they are present, the organic compound(s) (II) generally represent from 0.1 to 20% and preferably from 1% to 5% by weight relative to the total weight of the composition.

The composition according to the invention may also comprise one or more additional dyes. In particular, the composition according to the invention may also comprise at least one additional dye, other than dyes of hydrophobic nature with a log P of greater than or equal to 2, chosen from natural dyes and nonnatural direct dyes, oxidation dye precursors, and combinations thereof.

The term "natural dye" means any dye or dye precursor that is naturally occurring and that is produced either by extraction, and possible purification, from a plant matrix, or via chemical synthesis.

The additional natural dyes that are in particular suitable for use in the invention may be chosen, for example, from carminic acid, kermesic acid, isatin, chlorophyllines, haematin, haematoxylin, brazilin, brazileine, betanin, flavonoids and anthocyans.

Extracts or decoctions containing these natural dyes, and in particular henna-based extracts, may also be used.

The composition may also comprise one or more additional nonnatural direct dyes, other than the dyes of hydrophobic nature described above, and chosen from ionic or nonionic species, preferably cationic or nonionic species.

Examples of suitable additional direct dyes that may be mentioned include the following direct dyes: azo dyes; methine dyes; carbonyl dyes; azine dyes; nitro(hetero)aryl dyes; tri(hetero)arylmethane dyes; porphyrin dyes and phthalocyanin dyes, alone or as mixtures.

More particularly, the azo dyes comprise an —N=N— function in which the two nitrogen atoms are not simultaneously engaged in a ring. However, it is not excluded for one of the two nitrogen atoms of the sequence —N=N— to be engaged in a ring.

The dyes of the methine family are more particularly compounds comprising at least one sequence selected from >C=C< and —N=C< in which the two atoms are not simultaneously engaged in a ring. However, it is pointed out that one of the nitrogen or carbon atoms of the sequences may be engaged in a ring. More particularly, the dyes of this family are derived from compounds of true methine type, comprising one or more above-mentioned sequences —C=C—, of azomethine type, comprising at least one, or more, sequences —C=N— with, for example, azacarbocyanins and their isomers, diazacarbocyanins and their isomers, and tetraazacarbocyanins; of mono- and diarylmethane type; of indoamine or diphenylamine type; of indophenol type; or of indoaniline type.

As regards the dyes of the carbonyl family, examples that may be mentioned include nonnatural dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, naphthalimide, anthrapyrimidine, diketopyrrolopyrrole and coumarin.

As regards the dyes of the cyclic azine family, mention may be made especially of azine, xanthene, thioxanthene, fluorindine, acridine, (di)oxazine, (di)thiazine and pyronin.

The nitro(hetero)aromatic dyes are more particularly nitrobenzene or nitropyridine direct dyes.

As regards the dyes of porphyrin or phthalocyanin type, it is possible to use cationic or non-cationic compounds, optionally comprising one or more metals or metal ions, for instance alkali metals, alkaline-earth metals, zinc and silicon.

Examples of particularly suitable additional synthetic direct dyes that may be mentioned include nitrobenzene dyes; azo, azomethine, methine, azacarbocyanin such as tetraazacarbocyanin and tetraazapentamethine direct dyes, quinone direct dyes, and in particular anthraquinone, naphthoquinone or benzoquinone dyes, azine, xanthene, triarylmethane and indoamine direct dyes, phthalocyanins and porphyrins, alone or as a mixture. Even more preferably, these additional direct dyes are selected from nitrobenzene dyes; azo, azomethine and methine direct dyes, tetraazacarbocyanins and tetraazapentamethines, alone or as a mixture.

These dyes may be monochromophoric dyes, i.e. comprising only one dye, or polychromophoric, preferably di- or trichromophoric, the chromophores possibly being identical or different, and from the same chemical family or otherwise. It should be noted that a polychromophoric dye comprises several radicals each derived from a molecule that absorbs in the visible region between 400 and 800 nm Furthermore, this absorbance of the dye does not require any prior oxidation thereof, or combination with any other chemical species.

In the case of polychromophoric dyes, the chromophores are connected together by means of at least one linker, which may be cationic or non-cationic.

Among the polychromophoric dyes, mention may be made more particularly of symmetrical or nonsymmetrical azo and/or azomethine (hydrazone) dichromophoric or trichromophoric dyes comprising, on the one hand, at least one optionally fused 5- or 6-membered aromatic heterocycle, comprising at least one quaternized nitrogen atom engaged in said heterocycle and optionally at least one other heteroatom (such as nitrogen, sulfur or oxygen), and, on the other hand, at least one optionally substituted phenyl or naphthyl group, optionally bearing at least one group OR with R representing a hydrogen atom, an optionally substituted $C_1$-$C_6$ alkyl radical, an optionally substituted phenyl nucleus, or at least one group $N(R')_2$ with R', which may be identical or different, representing a hydrogen atom, an optionally substituted $C_1$-$C_6$ alkyl radical or an optionally substituted phenyl nucleus; the radicals R' possibly forming, with the nitrogen atom to which they are attached, a saturated 5- or 6-membered heterocycle, or alternatively one and/or both the radicals R' may each form, with the carbon atom of the aromatic ring located ortho to the nitrogen atom, a saturated 5- or 6-membered heterocycle.

Aromatic cationic heterocycles that may preferably be mentioned include 5- or 6-membered rings containing 1 to 3 nitrogen atoms and preferably 1 or 2 nitrogen atoms, one being quaternized; said heterocycle moreover being optionally fused to a benzene nucleus. It should similarly be noted that the heterocycle may optionally comprise another heteroatom other than nitrogen, for instance sulfur or oxygen.

If the heterocycles or phenyl or naphthyl groups are substituted, they are substituted, for example, with one or more $C_1$-$C_8$ alkyl radicals optionally substituted with a hydroxyl, $C_1$-$C_2$ alkoxy, $C_2$-$C_4$ hydroxyalkoxy, acetylamino or amino group substituted with one or two $C_1$-$C_4$ alkyl radicals, optionally bearing a hydroxyl group, or the two radicals possibly forming, with the nitrogen atom to which they are attached, a 5- or 6-membered heterocycle optionally comprising another heteroatom identical to or different than nitrogen; a halogen atom; a hydroxyl group; a $C_1$-$C_2$ alkoxy radical; a $C_2$-$C_4$ hydroxyalkoxy radical; an amino radical; an amino radical substituted with one or two identical or different $C_1$-$C_4$ alkyl radicals optionally bearing a hydroxyl group.

Preferably, the linker is a linear, branched or cyclic $C_1$-$C_{20}$ alkyl chain, optionally interrupted with at least one heteroatom, such as nitrogen or oxygen, and/or with at least one group comprising CO or $SO_2$, optionally interrupted with at least one substituted or unsubstituted phenyl or naphthyl group, optionally interrupted with at least one saturated, unsaturated or aromatic heterocycle that may or may not be fused to a phenyl nucleus, said heterocycle comprising at least one quaternized nitrogen atom engaged in said ring and optionally at least one other heteroatom, such as oxygen, nitrogen or sulfur, optionally interrupted with at least one quaternary ammonium group substituted with two $C_1$-$C_{15}$ alkyl groups; the linker not comprising any nitro, nitroso or peroxy groups.

If the heterocycles or aromatic nuclei are substituted, they are substituted, for example, with one or more $C_1$-$C_8$ alkyl radicals optionally substituted with a hydroxyl, $C_1$-$C_2$ alkoxy, $C_2$-$C_4$ hydroxyalkoxy, acetylamino or amino group substituted with one or two identical or different $C_1$-$C_4$ alkyl radicals, optionally bearing a hydroxyl group, or the two radicals possibly forming, with the nitrogen atom to which they are attached, a 5- or 6-membered heterocycle optionally comprising another heteroatom identical to or different than nitrogen, a halogen atom; a hydroxyl group, a $C_1$-$C_2$ alkoxy radical; a $C_2$-$C_4$ hydroxyalkoxy radical, an amino radical, an amino radical substituted with one or two identical or different $C_1$-$C_4$ alkyl radicals optionally bearing a hydroxyl group.

The bonding between the linker and each chromophore generally takes place via a heteroatom substituent on the phenyl or naphthyl nucleus or via the quaternized nitrogen atom of the cationic heterocycle.

Among the azo, azomethine, methine and tetraazapentamethine monochromophoric direct dyes that may be used according to the invention, mention may be made of the cationic dyes described in patent applications WO 95/15144, WO 95/01772 and EP 714 954; FR 2 189 006, FR 2 285 851, FR 2 140 205, EP 1 378 544 and EP 1 674 073.

Thus, mention may be made especially of the cationic direct dyes corresponding to the following formulae:

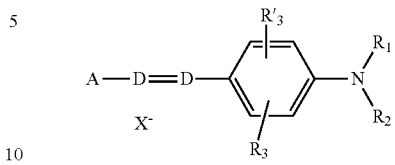

in which:

D represents a nitrogen atom or the —CH group, $R_1$ and $R_2$, which may be identical or different, represent a hydrogen atom, a $C_1$-$C_4$ alkyl radical which may be substituted with a —CN, —OH or —$NH_2$ radical, or form, with a carbon atom of the benzene ring, an optionally oxygenous or nitrogenous heterocycle which may be substituted with one or more $C_1$-$C_4$ alkyl radicals; a 4'-aminophenyl radical, $R_3$ and $R'_3$, which may be identical or different, represent a hydrogen atom or a halogen atom chosen from chlorine, bromine, iodine and fluorine, or a cyano, $C_1$-$C_4$ alkyl, $C_1$-$C_4$ alkoxy or acetyloxy radical, $X^-$ represents an anion preferably selected from chloride, methyl sulfate and acetate, A represents a group selected from the following structures:

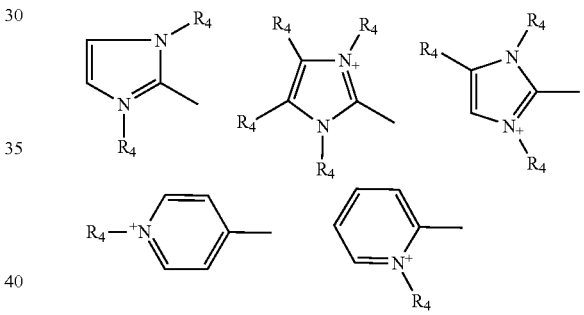

in which $R_4$ represents a $C_1$-$C_4$ alkyl radical which may be substituted with a hydroxyl radical;

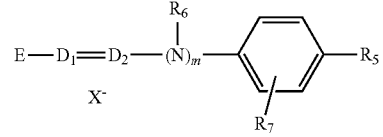

in which:

$R_5$ represents a hydrogen atom, a $C_1$-$C_4$ alkoxy radical or a halogen atom such as bromine, chlorine, iodine or fluorine, $R_6$ represents a hydrogen atom or a $C_1$-$C_4$ alkyl radical or forms, with a carbon atom of the benzene ring, a heterocycle which optionally contains oxygen and/or is substituted with one or more $C_1$-$C_4$ alkyl groups, $R_7$ represents a hydrogen or halogen atom such as bromine, chlorine, iodine or fluorine;

$D_1$ and $D_2$, which may be identical or different, represent a nitrogen atom or a —CH group, m=0 or 1, $X^-$ represents a cosmetically acceptable anion which is preferably selected from chloride, methyl sulfate and acetate, E represents a group selected from the following structures:

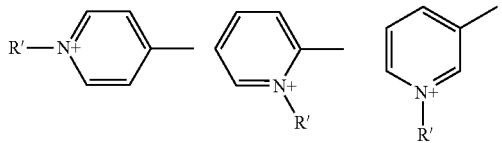

in which R' represents a $C_1$-$C_4$ alkyl radical.

When m=0 and when $D_1$ represents a nitrogen atom, E may then also denote a group of the following structure:

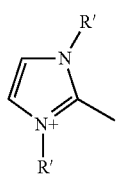

in which R' represents a $C_1$-$C_4$ alkyl radical.

Among the abovementioned compounds, use is made most particularly of the following compounds:

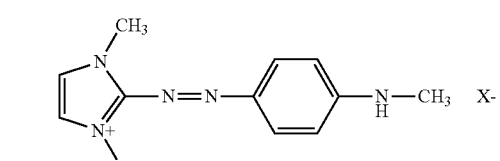

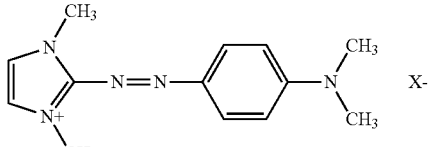

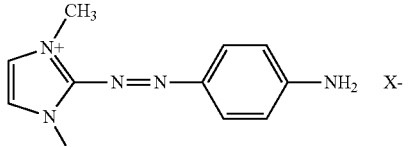

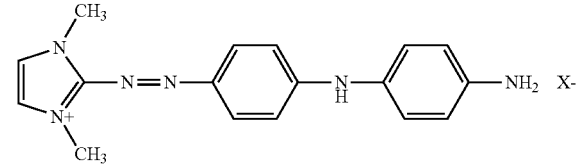

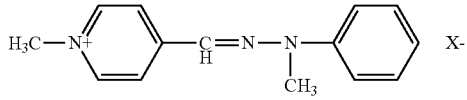

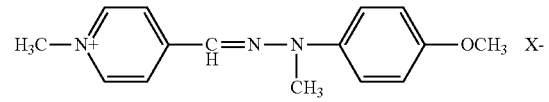

The tetraazapentamethine dyes that can be used according to the invention include the following compounds appearing in the table below:

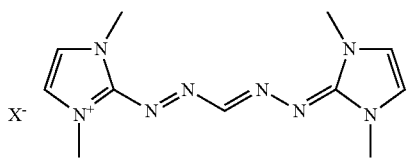

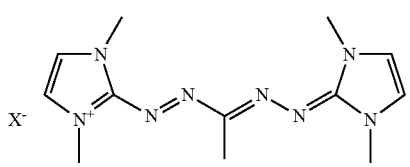

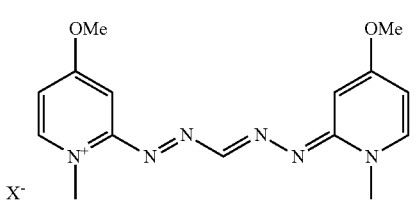 [SMILES: "X-" ; COc1cc[n+](C)c(/N=N/C=N/N=c2\cc(OC)ccn2C)c1]

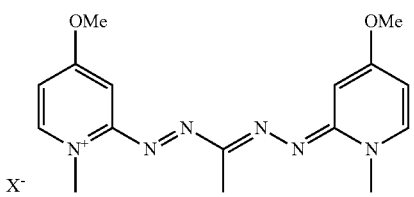 [SMILES: "X-" ; COc1cc[n+](C)c(/N=N/C(C)=N/N=c2\cc(OC)ccn2C)c1]

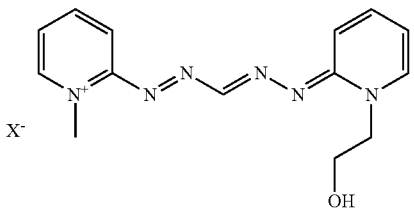 [SMILES: "X-" ; C[n+]1ccccc1/N=N/C=N/N=c1\ccccn1CCO]

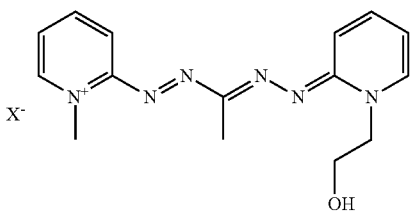

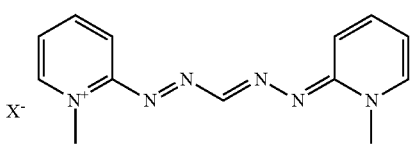

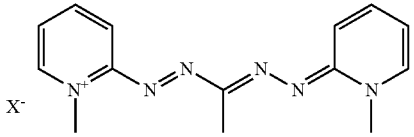

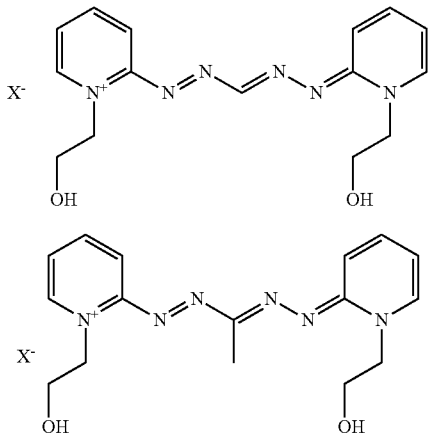

X⁻ represents an anion preferably selected from chloride, iodide, methyl sulfate, ethyl sulfate and acetate.

The dye composition may also comprise one or more oxidation dye precursors, more particularly one or more oxidation bases optionally combined with one or more couplers.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylene-diamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols, mention may be made of para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino 1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl 3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. 4,5-Diamino-1-(β-methoxyethyl)pyrazole may also be used.

Pyrazole derivatives that may also be mentioned include diamino-N,N-dihydropyrazolopyrazolones and especially those described in patent application FR 2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-bis(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

Heterocyclic bases that will preferentially be used include 4,5-diamino-1-(β-hydroxyethyl)pyrazole and/or 2,3-diamino-6,7-dihydro-1H,5H-pyrazolo[1,2-a]-pyrazol-1-one and the addition salts thereof.

The composition according to the invention may optionally comprise one or more couplers advantageously chosen from those conventionally used in the dyeing of keratin fibers.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazole-5-one, 1-phenyl-3-methylpyrazole-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, addition salts thereof, and mixtures thereof.

In general, the addition salts of the oxidation bases and couplers that may be used in the context of the invention are especially selected from the addition salts with an acid such as the hydrochlorides, hydrobromides, sulfates, citrates, succinates, tartrates, lactates, tosylates, benzenesulfonates, phosphates and acetates.

The oxidation base(s), when they are present in the composition, advantageously represent from 0.0001% to 10% by weight relative to the weight of the composition, and preferably from 0.005% to 5% by weight relative to the weight of the composition.

The coupler(s), if they are present, advantageously represent from 0.0001% to 10% by weight relative to the weight of the composition, and preferably from 0.005% to 5% by weight relative to the weight of the composition.

When they are present, the additional dye(s) represent from 0.01% to 10% by weight and preferably from 0.5% to 5% by weight relative to the weight of the composition.

The dye composition according to the invention may also comprise one or more conditioning agents.

Examples that may be mentioned include volatile or nonvolatile, linear, cyclic, branched or unbranched silicones. The silicones may be in the form of oils, resins or gums, and they may in particular be polyorganosiloxanes that are insoluble in the cosmetically acceptable medium.

Organopolysiloxanes are defined in greater detail in Walter Noll's *Chemistry and Technology of Silicones* (1968) Academic Press. They may be volatile or nonvolatile.

When they are volatile, the silicones are more particularly chosen from those with a boiling point of between 60° C. and 260° C.

Conditioning agents that may also be used include cationic polymers such as Polyquaterniums 22, 6, 10, 11, 35 and 37, and hexadimethrine chloride.

The concentration of conditioning agent(s) in the composition(s) that are useful in the invention may range from 0.01% to 10% by weight, preferably from 0.05% to 5% by weight and more preferentially from 0.1% to 3% by weight relative to the total weight of the composition.

The composition according to the invention may also comprise one or more organic thickeners.

The organic thickeners may be chosen from fatty acid amides such as coconut monoethanolamide or diethanolamide and oxyethylenated carboxylic acid monoethanolamide alkyl ether, polymeric thickeners such as cellulose-based thickeners, in particular hydroxyethylcellulose, hydroxypropylcellulose or carboxymethylcellulose, guar gum and derivatives thereof such as hydroxypropyl guar, gums of microbial origin such as xanthan gum, scleroglucan gum, acrylic acid or acrylamidopropanesulfonic acid crosslinked homopolymers and associative polymers, i.e. polymers comprising hydrophilic regions and fatty-chain hydrophobic regions, which are capable, in an aqueous medium, of reversibly combining with each other or with other molecules.

According to one particular embodiment, the thickener is polymeric and is chosen from cellulose-based thickeners such as hydroxyethylcellulose, hydroxypropylcellulose or carboxymethylcellulose, guar gum and derivatives thereof such as hydroxypropyl guar, gums of microbial origin such as xanthan gum, scleroglucan gum, and acrylic acid or acrylamidopropanesulfonic acid crosslinked homopolymers.

As regards the associative thickeners, one or more polymers of nonionic or ionic nature, preferably anionic or cationic, may be used.

Their chemical structure more particularly comprises at least one hydrophilic region and at least one hydrophobic region. The term "hydrophobic group" means a radical or polymer with a saturated or unsaturated, linear or branched hydrocarbon-based chain, comprising at least 8 carbon atoms, preferably from 10 to 30 carbon atoms, in particular from 12 to 30 carbon atoms and more preferentially from 18 to 30 carbon atoms.

Preferentially, the hydrocarbon-based group is derived from a monofunctional compound. By way of example, the hydrophobic group may be derived from a fatty alcohol such as stearyl alcohol, dodecyl alcohol or decyl alcohol. It may also denote a hydrocarbon-based polymer, for instance polybutadiene.

Among the anionic amphiphilic polymers comprising at least one hydrophobic or fatty chain, mention may be made of:

(I) polymers comprising at least one hydrophilic unit, and at least one fatty-chain allyl ether unit, more particularly those whose hydrophilic unit is formed by an unsaturated ethylenic anionic monomer, advantageously by a vinylcarboxylic acid and most particularly by an acrylic acid or a methacrylic acid or mixtures thereof, and whose fatty-chain allyl ether unit corresponds to the monomer of formula (A) below:

$$CH_2=CR'CH_2OB_nR \quad (A)$$

in which R' denotes H or $CH_3$, B denotes an ethyleneoxy radical, n is zero or denotes an integer ranging from 1 to 100, R denotes a hydrocarbon-based radical chosen from alkyl, arylalkyl, aryl, alkylaryl and cycloalkyl radicals, comprising from 8 to 30 carbon atoms, preferably 10 to 24 and even more particularly from 12 to 18 carbon atoms. A unit of formula (A) that is more particularly preferred is a unit in which R' denotes H, n is equal to 10, and R denotes a $C_{18}$ stearyl radical.

Among these fatty-chain anionic polymers, those that are preferred are polymers formed from 20% to 60% by weight of acrylic acid and/or methacrylic acid, 5% to 60% by weight of lower alkyl(meth)acrylates, 2% to 50% by weight of fatty-chain allyl ether of formula (A), and 0 to 1% by weight of a crosslinking agent that is a well-known copolymerizable polyethylenically unsaturated monomer, for instance diallyl phthalate, allyl(meth)acrylate, divinylbenzene, (poly)ethylene glycol dimethacrylate or methylenebisacrylamide.

Among the latter polymers, the ones that are most particularly preferred are crosslinked terpolymers of methacrylic acid, of ethyl acrylate, of polyethylene glycol (10 EO) stearyl ether such as Steareth 10, especially those sold by the company Allied Colloids under the names Salcare SC 80 and Salcare SC 90, which are aqueous emulsions containing 30% of a crosslinked terpolymer of methacrylic acid, of ethyl acrylate and of stearth-10 alkyl ether (40/50/10).

(II) polymers comprising at least one hydrophilic unit of unsaturated olefinic carboxylic acid type, and at least one hydrophobic unit of the type such as a $C_{10}$-$C_{30}$ alkyl ester of an unsaturated carboxylic acid.

These polymers are preferably chosen from those in which the hydrophilic unit of unsaturated olefinic carboxylic acid type corresponds to the monomer of formula (B) below:

$$CH_2=C-C-OH \quad (B)$$
$$\quad | \quad ||$$
$$\quad R_1 \quad O$$

in which $R_1$ denotes H or $CH_3$ or $C_2H_5$, i.e. acrylic acid, methacrylic acid or ethacrylic acid units, and whose hydrophobic unit of the type such as a $C_{10}$-$C_{30}$ alkyl ester of an unsaturated carboxylic acid corresponds to the monomer of formula (C)

$$CH_2=C-C-OR_3 \quad (C)$$
$$\quad | \quad ||$$
$$\quad R_2 \quad O$$

in which $R_2$ denotes H or $CH_3$ or $C_2H_5$, i.e. acrylate, methacrylate or ethacrylate units, and preferably H, i.e. acrylate units, or $CH_3$, i.e. methacrylate units, $R_3$ denoting a $C_{10}$-$C_{30}$ and preferably $C_{12}$-$C_{22}$ alkyl radical.

The $C_{10}$-$C_{30}$ alkyl esters of unsaturated carboxylic acids are, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Among the fatty-chain anionic polymers of this type, the ones that will be used more particularly are polymers formed from a mixture of monomers comprising:

(i) essentially acrylic acid, (ii) an ester of formula (C) described above and in which $R_2$ denotes H or $CH_3$, $R_3$ denoting an alkyl radical containing from 12 to 22 carbon atoms, (iii) and a crosslinking agent, which is a well-known copolymerizable polyethylenic unsaturated monomer, for instance diallyl phthalate, allyl(meth)acrylate, divinylbenzene, (poly)ethylene glycol dimethacrylate or methylenebis acrylamide.

Among the fatty-chain anionic polymers of this type, use will be made more particularly of those formed from 95% to 60% by weight of acrylic acid, which correspond to the hydrophilic unit, 4% to 40% by weight of $C_{10}$-$C_{30}$ alkyl acrylate, which correspond to the hydrophobic unit, and 0 to 6% by weight of crosslinking polymerizable monomer, or alternatively those formed from 98% to 96% by weight of acrylic acid, which correspond to the hydrophilic unit, 1% to 4% by weight of $C_{10}$-$C_{30}$ alkyl acrylate, which correspond to the hydrophobic unit, and 0.1% to 0.6% by weight of crosslinking polymerizable monomer such as those described previously.

Among said polymers above, the ones most particularly preferred according to the present invention are the products sold by the company Goodrich under the trade names Pemulen TR1, Pemulen TR2, Carbopol 1382, and even more preferentially Pemulen TR1, and the product sold by the company SEPPIC under the name Coatex SX.

(III) maleic anhydride/$C_{30}$-$C_{38}$ α-olefin/alkyl maleate terpolymers, such as the product (maleic anhydride/$C_{30}$-$C_{38}$ α-olefin/isopropyl maleate) sold under the name Performa V 1608 by the company Newphase Technologies.

(IV) acrylic terpolymers comprising:

(a) from 20% to 70% by weight of an α,β-monoethylenically unsaturated carboxylic acid, (b) from 20% to 80% by weight of a nonsurfactant α,β-monoethylenically unsaturated monomer other than (a), (c) from 0.5% to 60% by weight of a nonionic monourethane, which is the product of reaction of a monohydric surfactant with a monoethylenically unsaturated monoisocyanate, such as those described in patent application EP-A-0 173 109 and more particularly a methacrylic acid/methyl acrylate/dimethyl meta-isopropenylbenzylisocyanate terpolymer of ethoxylated behenyl alcohol (40 OE) as a 25% aqueous dispersion.

(V) copolymers comprising among their monomers an α,β-monoethylenically unsaturated carboxylic acid and an ester of an α,β-monoethylenically unsaturated carboxylic acid and of an oxyalkylenated ($C_8$-$C_{30}$) fatty alcohol.

Preferentially, these compounds also comprise as monomer an ester of an α,β-monoethylenically unsaturated carboxylic acid and of a $C_1$-$C_4$ alcohol.

An example of a compound of this type that may be mentioned is Aculyn 22 sold by the company Röhm & Haas, which is a methacrylic acid/ethyl acrylate/oxyalkylenated stearyl methacrylate terpolymer.

The hydrophobic or fatty-chain nonionic amphiphilic polymers are preferably chosen from:

(1) celluloses modified with groups comprising at least one fatty chain, especially such as:
hydroxyethylcelluloses modified with groups comprising at least one fatty chain, such as alkyl, arylalkyl or alkylaryl groups, or mixtures thereof, and in which the alkyl groups are preferably $C_8$-$C_{22}$, for instance the product Natrosol Plus Grade 330 CS($C_{16}$ alkyl) sold by the company Aqualon, or the product Bermocoll EHM 100 sold by the company Berol Nobel,
celluloses modified with alkylphenyl polyalkylene glycol ether groups, such as the product Amercell Polymer HM1500 (nonylphenyl polyethylene glycol (15) ether) sold by the company Amerchol, (2) hydroxypropyl guars modified with groups comprising at least one fatty chain, such as the product Esaflor HM 22 ($C_{22}$ alkyl chain) sold by the company Lamberti, and the products RE210-18 ($C_{14}$ alkyl chain) and RE205-1 ($C_{20}$ alkyl chain) sold by the company Rhone-Poulenc, (3) copolymers of vinylpyrrolidone and of fatty-chain hydrophobic monomers, for instance:
the products Antaron V216 or Ganex V216, which are vinylpyrrolidone/hexadecene copolymer, sold by the company ISP,
the products Antaron V220 or Ganex V220, which are vinylpyrrolidone/hexadecene copolymer, sold by the company ISP, (4) copolymers of $C_1$-$C_6$ alkyl methacrylates or acrylates and of amphiphilic monomers comprising at least one fatty chain, for instance the oxyethylenated methyl acrylate/stearyl acrylate copolymer sold by the company Goldschmidt under the name Antil 208, (5) copolymers of hydrophilic methacrylates or acrylates and of hydrophobic monomers comprising at least one fatty chain, for instance the polyethylene glycol methacrylate/lauryl methacrylate copolymer, (6) polymers with an aminoplast ether backbone bearing at least one fatty chain, such as the Pure Thix compounds sold by the company Sud-Chemie, (7) polyurethane polyethers comprising in their chain both hydrophilic blocks usually of polyoxyethylenated nature and hydrophobic blocks, which may be aliphatic sequences alone and/or cycloaliphatic and/or aromatic sequences.

Preferably, the polyurethane polyethers comprise at least two hydrocarbon-based fatty chains containing from 8 to 30 carbon atoms, separated by a hydrophilic block, the hydrocarbon-based chains possibly being pendent chains or chains at the end of the hydrophilic block.

As examples of fatty-chain nonionic polyurethane polyethers that may be used in the invention, use may be made of Rheolate 205 containing a urea function, sold by the company Rheox, or Rheolate 208, 204 or 212, and also Acrysol RM 184, Aculyn or Acrysol 44 and Aculyn or Acrysol 46 from the company Röhm & Haas, Aculyn 46 being a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%), Aculyn 44 being a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%).

Mention may also be made of the product Elfacos T210 containing a $C_{12}$-$C_{14}$ alkyl chain and the product Elfacos T212 containing a $C_{18}$ alkyl chain, from Akzo, and also the product DW 1206B from Röhm & Haas, containing a $C_{20}$ alkyl chain and a urethane bond, sold at a solids content of 20% in water.

It is also possible to use solutions or dispersions of these polymers, especially in water or in aqueous-alcoholic medium. Examples of such polymers that may be mentioned are Rheolate 255, Rheolate 278 and Rheolate 244 sold by the company Rheox. The products DW 1206F and DW 1206J sold by the company Röhm & Haas may also be used.

The polyurethane polyethers that may be used according to the invention are in particular those described in the article by G. Formum, J. Bakke and F k. Hansen—Colloid Polym. Sci 271, 380.389 (1993).

The cationic amphiphilic polymers used comprising at least one hydrophobic or fatty chain may especially be chosen from quaternized cellulose derivatives, cationic polyurethanes and cationic polyvinyllactams, and preferably from quaternized cellulose derivatives.

As examples of polymers of this type, mention may be made in particular of:
quaternized celluloses modified with groups comprising at least one fatty chain, such as alkyl, arylalkyl or alkylaryl groups comprising at least 8 carbon atoms, and mixtures thereof,
quaternized hydroxyethylcelluloses modified with groups comprising at least one fatty chain, such as alkyl, arylalkyl or alkylaryl groups comprising at least 8 carbon atoms, and mixtures thereof.

The alkyl radicals borne by the above quaternized celluloses or hydroxyethylcelluloses preferably comprise from 8 to 30 carbon atoms. The aryl radicals preferably denote phenyl, benzyl, naphthyl or anthryl groups.

Examples of quaternized alkylhydroxyethylcelluloses containing $C_8$-$C_{30}$ fatty chains that may be indicated include the products Quatrisoft LM 200, Quatrisoft LM-X529-18-A, Quatrisoft LM-X529-18B ($C_{12}$ alkyl) and Quatrisoft LM-X529-8 ($C_{18}$ alkyl) sold by the company Amerchol and the products Crodacel QM, Crodacel QL ($C_{12}$ alkyl) and Crodacel QS ($C_{18}$ alkyl) sold by the company Croda.

The content of thickening polymers, if they are present, usually ranges from 0.05% to 5% by weight relative to the weight of the dye composition.

According to one particularly advantageous embodiment, the dye composition according to the invention comprises one or more surfactants. These surfactants may be chosen, indiscriminantly, alone or as mixtures, from anionic, amphoteric, nonionic, zwitterionic and cationic surfactants.

As regards the anionic surfactants, use is usually made of salts, in particular alkali metal salts such as sodium salts, ammonium salts, amine salts, amino alcohol salts or alkaline-earth metal salts, for example magnesium salts, and the salts of the following compounds, alone or as a mixture:
alkyl sulfates, alkyl ether sulfates, alkylamido ether sulfates, alkylaryl polyether sulfates, alkylsulfonates, alkylamidesulfonates, alkylarylsulfonates, alkylsulfosuccinates, alkyl ether sulfosuccinates, alkylamidesulfosuccinates, alkylsulfoacetates, acylsarcosinates, acylglutamates, alkyl esters of polyglycoside carboxylic acids such as alkyl glucoside citrates, alkyl polyglycoside tartrates and alkyl polyglycoside sulfosuccinates, alkylsulfosuccinamates, acylisethionates, N-acyltaurates, acyllactylates, alkyl-D-galactoside uronic acids, polyoxyalkylenated alkyl ether carboxylic acids, polyoxyalkylenated alkylaryl ether carboxylic acids, polyoxyalkylenated alkylamido ether carboxylic acids, the alkyl or acyl (RCO—) group of these compounds comprising from 10 to 24 carbon atoms and the aryl group preferably denoting a phenyl or benzyl group, and the number of oxyalkylene and preferably oxyethylene groups is between 2 and 50.

As regards the nonionic surfactants, they may advantageously be chosen from the following compounds, alone or as a mixture:

polyethoxylated, polypropoxylated or polyglycerolated fatty alcohols, polyethoxylated, polypropoxylated or polyglycerolated alpha-diols, the number of ethylene oxide or propylene oxide groups ranging from 2 to 50, and the number of glycerol groups ranging from 2 to 30, condensates of ethylene oxide and propylene oxide with fatty alcohols, polyethoxylated fatty amides containing from 2 to 30 mol of ethylene oxide, polyglycerolated fatty amides comprising from 1 to 5 glycerol groups, polyethoxylated fatty amides containing from 2 to 30 mol of ethylene oxide, ethoxylated fatty acid esters of sorbitan containing from 2 to 30 mol of ethylene oxide, fatty acid esters of sucrose, alkylpolyglucosides, N-alkylglucamine derivatives, these compounds comprising at least one alkyl or alkenyl chain comprising 10 to 24 carbon atoms, copolymers of ethylene oxide and of propylene oxide.

The cationic surfactants included in the composition according to the invention may be chosen especially from the following compounds, alone or as a mixture:

optionally polyethoxylated (2 to 30 mol of ethylene oxide) primary, secondary or tertiary fatty amines, and salts thereof, quaternary ammonium salts, such as tetraalkylammonium, alkylamidoalkyltrialkylammonium, trialkylbenzylammonium, trialkylhydroxyalkylammonium and alkylpyridinium chlorides and bromides, alkylimidazoline derivatives, these compounds comprising at least one alkyl chain comprising 10 to 24 carbon atoms.

Finally, the amphoteric surfactants may be chosen from the following compounds, alone or as mixtures:

secondary or tertiary aliphatic amine derivatives in which the aliphatic group is a linear or branched chain containing from 10 to 24 carbon atoms and comprising at least one water-solubilizing anionic group, for instance a carboxylate, sulfonate, sulfate, phosphate or phosphonate group, alkylbetaines, sulfobetaines, alkylamido($C_6$-$C_8$)alkylbetaines, alkylamido($C_6$-$C_8$)alkylsulfobetaines, these compounds comprising at least one alkyl chain comprising from 10 to 24 carbon atoms.

Preferably, the surfactants are nonionic, anionic or amphoteric and even more preferably nonionic.

Usually, the surfactants represent an amount of from 0.01% to 50% by weight and preferably from 0.1% to 25% by weight relative to the weight of the composition.

The dye composition according to the invention may also comprise various adjuvants conventionally used in hair dye compositions, for instance cationic, anionic, nonionic, amphoteric or zwitterionic polymers other than the thickeners mentioned previously, and mixtures thereof; mineral thickeners especially such as clays; antioxidants, for instance ascorbic acid or erythorbic acid; reducing agents other than the compounds (I) mentioned previously, such as, inter alia, erythorbic acid, reducing sugars, penetrants, sequestrants, for instance ethylenediaminetetraacetic acid or salts thereof, fragrances, matting agents with, for example, titanium oxides, buffers, dispersants, film-forming agents, ceramides and preserving agents.

The above adjuvants are generally present in an amount, for each of them, of between 0.01% and 20% by weight, relative to the weight of the composition.

The composition according to the invention comprises a cosmetically acceptable medium.

The cosmetically acceptable medium of the composition, which is a medium that is suitable for dyeing human keratin fibers, preferably comprises water and optionally one or more organic solvents other than the organic compounds (II) and other than the compounds (I) mentioned previously.

Examples of such organic solvents that may be mentioned include linear or branched $C_2$-$C_4$ alkanols, such as ethanol and isopropanol, polyols and polyol ethers, for instance 2-butoxyethanol, hexylene glycol, propylene glycol, dipropylene glycol and glycerol, and mixtures thereof.

These organic solvent(s) may be present in proportions preferably ranging from 1% to 40% by weight relative to the total weight of the dye composition, and even more preferentially from 5% to 30% by weight.

The amount of water in the composition according to the invention is preferably greater than 10% by weight, and even more advantageously greater than or equal to 25% by weight. Preferably, the water content is between 25% and 98% by weight, relative to the weight of the composition.

The pH of the composition according to the invention may be between 2 and 12, limits inclusive. The pH of the composition according to the invention is preferably between 8 and 12, limits inclusive.

It may be adjusted to the desired value by means of one or more acidifying agents.

Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

The composition according to the invention may also comprise one or more oxidizing agents.

In particular, the composition with the oxidizing agent is obtained by the extemporaneous mixing, before application, of a composition described previously with at least one composition comprising one or more oxidizing agents.

The oxidizing agent is preferably chosen from hydrogen peroxide, urea peroxide, alkali metal bromates or ferricyanides, peroxygenated salts, for instance persulfates, perborates and percarbonates of alkali metals or alkaline-earth metals, such as sodium, potassium and magnesium.

The use of hydrogen peroxide is particularly preferred.

This oxidizing agent is advantageously formed by hydrogen peroxide in aqueous solution (aqueous hydrogen peroxide solution), the titer of which may range more particularly from 1 to 40 volumes and even more preferentially from 5 to 40 volumes.

The compositions according to the invention may result from the extemporaneous mixing of several compositions.

Another subject of the invention thus consists of a process for dyeing keratin fibers, especially human keratin fibers such as the hair, which consists in applying the composition according to the invention described previously.

In accordance with a first embodiment, the applied composition does not comprise any oxidizing agent. This embodiment is especially suitable in the case where the composition does not comprise an oxidation dye precursor (bases or coupler).

In accordance with a second embodiment, the composition is applied in the presence of at least one oxidizing agent.

This embodiment may be used if the composition comprises as dyes only direct dyes or dyes of hydrophobic nature, and optionally one or more additional direct dyes, or alternatively if the composition comprises one or more dyes of hydrophobic nature, optionally one or more additional synthetic and/or natural direct dyes combined with one or more oxidation dye precursors (bases and couplers).

According to a first variant of this second embodiment, the composition that has just been detailed and that is obtained by extemporaneous mixing, before application, of a composition according to the invention free of oxidizing agent with an oxidizing composition, is applied to the fibers.

According to a second variant of this second embodiment, the composition according to the invention, free of oxidizing agent, and an oxidizing composition are applied successively and without intermediate rinsing.

The oxidizing composition used comprises one or more oxidizing agents as defined above.

As regards the organic solvents that may be present in the oxidizing composition, reference may be made to the list indicated previously in the context of the description of the composition according to the invention. These organic solvents may also be chosen from the organic compounds (II) present in the composition according to the invention, with the Hansen solubility parameter δH of less than or equal to 16 MPa$^{1/2}$ and with a molecular weight of less than 250 g/mol and other than the compounds (I) mentioned previously.

The oxidizing composition may take the form of a solution, an emulsion or a gel.

It may optionally comprise one or more additives conventionally used in the field of dyeing human keratin fibers, as a function of the desired galenical form. Once again, reference may be made to the list of additives given above.

Irrespective of the embodiment selected (with or without oxidizing agent), the mixture applied to the keratin fibers is left in place for a time generally from about 1 minute to 1 hour and preferably from 10 minutes to 30 minutes.

The temperature during the process is conventionally between 10 and 200° C. and more particularly between room temperature (between 15 and 25° C.) and 80° C. and preferably between room temperature and 60° C.

At the end of the treatment, the human keratin fibers are optionally rinsed with water, washed with shampoo, rinsed again with water, and then dried or left to dry.

A subject of the invention is also a multi-compartment dyeing device or "kit", in which a first compartment contains the dye composition according to the present invention as described above, with the exception of the oxidizing agent(s), and a second compartment contains a composition comprising one or more oxidizing agents as described above.

The examples that follow are intended to illustrate the invention without, however, limiting its scope.

In these examples, all the amounts are indicated as weight percentages of active material relative to the total weight of the composition, unless otherwise indicated.

Example 1

The dye compositions according to the invention, the formulations of which are given in Table 1 below, are prepared.

TABLE 1

|  | 1 | 2 | 3 | 4 | 5 |
|---|---|---|---|---|---|
| Indigo [1] | 1 g | — | — | — | — |
| Isoindigo [2] | — | 1 g | — | — | — |
| Shellfish red [3] | — | — | 1 g | — | — |
| Thioindigo [4] | — | — | — | 1 g | — |
| Oralith [5] | — | — | — | — | 1 g |
| Benzyl alcohol | 5 g | 5 g | 5 g | 5 g | 5 g |
| Ethanol | 15 g | 15 g | 15 g | 15 g | 15 g |
| Acetoin | 1 g | 1 g | 1 g | 1 g | 1 g |
| Sodium carbonate | 2 g | 2 g | 2 g | 2 g | 2 g |
| Water | qs 100 g | qs 100 g | qs 100 g | qs 100 g | qs 100 g |

[1] Indigo, CAS = 482-89-3, sold by Sigma Aldrich
[2] Isoindigo
[3] Shellfish red, 6,6'-dibromoindigo sold by Kremer Pigmente
[4] Thioindigo, CAS = 522-75-8, sold by Sigma Aldrich
[5] Oralith, CAS = 2379-74-0, sold by Sigma Aldrich The compositions are left to stir under argon for 2 hours at 40° C.

The pH is then adjusted to 9.6 with 4 g of 25% aqueous ammonia solution and 4 g of aqueous 90% lactic acid solution.

Pairs of locks of natural and permanent-waved hair containing 90% white hair are dyed for 30 minutes at room temperature with each of these dye compositions 1 to 5, and the locks are then drained, rinsed, shampooed and dried.

Powerful and fast colorations are obtained.

Example 2

The dye compositions according to the invention, the formulations of which are given in Table 2 below, are prepared.

TABLE 2

|  | 6 | 7 | 8 | 9 | 10 |
|---|---|---|---|---|---|
| Indigo [1] | 1 g | — | — | — | — |
| Isoindigo [2] | — | 1 g | — | — | — |
| Shellfish red [3] | — | — | 1 g | — | — |
| Thioindigo [4] | — | — | — | 1 g | — |
| Oralith [5] | — | — | — | — | 1 g |
| Benzyl alcohol | 5 g | 5 g | 5 g | 5 g | 5 g |
| Ethanol | 15 g | 15 g | 15 g | 15 g | 15 g |
| Acetoin | 1 g | 1 g | 1 g | 1 g | 1 g |
| Sodium hydroxide | 2 g | 2 g | — | — | — |
| Potassium hydroxide | — | — | 2 g | 2 g | 2 g |
| Water | qs 100 g | qs 100 g | qs 100 g | qs 100 g | qs 100 g |

[1] Indigo, CAS = 482-89-3, sold by Sigma Aldrich
[2] Isoindigo
[3] Shellfish red, 6,6'-dibromoindigo sold by Kremer Pigmente
[4] Thioindigo, CAS = 522-75-8, sold by Sigma Aldrich
[5] Oralith, CAS = 2379-74-0, sold by Sigma Aldrich The compositions are left to stir under argon for 2 hours at 40° C.

The pH is then adjusted to 9.6 with 4 g of 25% aqueous ammonia solution and 4 g of aqueous 90% lactic acid solution.

Pairs of locks of natural and permanent-waved hair containing 90% white hair are dyed for 30 minutes at room temperature with each of these dye compositions 6 to 10, and the locks are then drained, rinsed, shampooed and dried.

Powerful and fast colorations are obtained.

Example 3

The dye compositions according to the invention, the formulations of which are given in Table 3 below, are prepared.

TABLE 3

|  | 11 | 12 | 13 |
|---|---|---|---|
| Indigo [1] | 1 g | 1 g | 1 g |
| Glutaroin | 1 g | — | — |
| Dihydroxyacetone | — | 1 g | — |
| Benzoin | — | — | 1 g |
| Benzyl alcohol | 5 g | 5 g | 5 g |
| Ethanol | 15 g | 15 g | 15 g |
| Sodium hydroxide | 2 g | 2 g | 2 g |
| Water | qs 100 g | qs 100 g | qs 100 g |

[1] Indigo, CAS = 482-89-3, sold by Sigma Aldrich

The compositions are prepared and applied to pairs of natural and permanent-waved locks of hair containing 90% white hairs, under the same conditions as in Example 2.

Powerful and fast blue colorations are obtained.

Example 4

The dye compositions according to the invention, the formulations of which are given in Table 4 below, are prepared.

TABLE 4

|  | 14 | 15 | 16 |
|---|---|---|---|
| Indigo [1] | 0.5 g | 0.5 g | 0.5 g |
| Curcumin | 0.5 g | 0.5 g | 0.5 g |
| Isatin | 0.3 g | 0.3 g | 0.3 g |
| Orcein | 0.3 g | 0.3 g | 0.3 g |
| Chlorophylline | 0.15 g | 0.15 g | 0.15 g |
| Sorghum | 0.02 g | 0.02 g | 0.02 g |
| Lactic acid | 0.01 g | 0.01 g | 0.01 g |
| Acetoin | 1 g | 1 g | 1 g |
| Ethanol | 15 g | 15 g | 15 g |
| Benzyl alcohol | 5 g | 1 g | — |
| 3-Phenyl-1-propanol | — | 0.5 g | — |
| Decanol | — | — | 5 g |
| CTAB [6] | — | — | 2 g |
| Sodium hydroxide | 2 g | 2 g | 2 g |
| Fragrance | qs | qs | qs |
| Water | qs 100 g | qs 100 g | qs 100 g |

[1] Indigo, CAS = 482-89-3, sold by Sigma Aldrich
[6] Cetyltrimethylammonium chloride The compositions are prepared and applied to pairs of natural and permanent-waved locks of hair containing 90% white hairs, under the same conditions as in Example 2.

Powerful and fast brown colorations are obtained.

Example 5

The dye compositions according to the invention, the formulations of which are given in Table 5 below, are prepared. The amounts of the constituents are expressed as weight percentages relative to the total weight of the composition.

TABLE 5

|  | 17 | 18 | 19 | 20 | 21 |
|---|---|---|---|---|---|
| Indigo [1] | 1 g | — | — | — | — |
| Isoindigo [2] | — | 1 g | — | — | — |
| Shellfish red [3] | — | — | 1 g | — | — |
| Thioindigo [4] | — | — | — | 1 g | — |
| Oralith [5] | — | — | — | — | 1 g |
| Benzyl alcohol | 5 g | 5 g | 5 g | 5 g | 5 g |
| Ethanol | 15 g | 15 g | 15 g | 15 g | 15 g |
| Acetoin | 1 g | 1 g | 1 g | 1 g | 1 g |

TABLE 5-continued

|  | 17 | 18 | 19 | 20 | 21 |
|---|---|---|---|---|---|
| Monoethanolamine | 2 g | 2 g | 2 g | 2 g | 2 g |
| Water | qs 100 g | qs 100 g | qs 100 g | qs 100 g | qs 100 g |

[1] Indigo, CAS = 482-89-3, sold by Sigma Aldrich
[2] Isoindigo
[3] Shellfish red, 6,6'-dibromoindigo sold by Kremer Pigmente
[4] Thioindigo, CAS = 522-75-8, sold by Sigma Aldrich
[5] Oralith, CAS = 2379-74-0, sold by Sigma Aldrich The compositions are left to stir under argon for 2 hours at 40° C.

The pH is then adjusted to 9.6 with 4 g of 25% aqueous ammonia solution and 4 g of aqueous 90% lactic acid solution.

Pairs of locks of natural and permanent-waved hair containing 90% white hair are dyed for 30 minutes at room temperature with each of these dye compositions 17 to 21, and the locks are then drained, rinsed, shampooed and dried.

Powerful and fast colorations are obtained.

Example 6

The dye compositions according to the invention, the formulations of which are given in Table 6 below, are prepared. The amounts are expressed in grams relative to 100 g of total weight of the composition.

TABLE 6

|  | 22 | 23 | 24 | 25 | 26 |
|---|---|---|---|---|---|
| Indigo [1] | 1 g | — | — | — | — |
| Isoindigo [2] | — | 1 g | — | — | — |
| Shellfish red [3] | — | — | 1 g | — | — |
| Thioindigo [4] | — | — | — | 1 g | — |
| Oralith [5] | — | — | — | — | 1 g |
| Benzyl alcohol | 5 g | 5 g | 5 g | 5 g | 5 g |
| Ethanol | 15 g | 15 g | 15 g | 15 g | 15 g |
| Acetoin | 1 g | 1 g | 1 g | 1 g | 1 g |
| Triethanolamine | 2 g | 2 g | 2 g | 2 g | 2 g |
| Water | qs 100 g | qs 100 g | qs 100 g | qs 100 g | qs 100 g |

[1] Indigo, CAS = 482-89-3, sold by Sigma Aldrich
[2] Isoindigo
[3] Shellfish red, 6,6'-dibromoindigo sold by Kremer Pigmente
[4] Thioindigo, CAS = 522-75-8, sold by Sigma Aldrich
[5] Oralith, CAS = 2379-74-0, sold by Sigma Aldrich The compositions are left to stir under argon for 2 hours at 40° C.

The pH is then adjusted to 9.6 with 4 g of 25% aqueous ammonia solution and 4 g of aqueous 90% lactic acid solution.

Pairs of locks of natural and permanent-waved hair containing 90% white hair are dyed for 30 minutes at room temperature with each of these dye compositions 22 to 26, and the locks are then drained, rinsed, shampooed and dried.

Powerful and fast colorations are obtained.

Example 7

The dye compositions according to the invention, the formulations of which are given in Table 7 below, are prepared.

The amounts of the constituents are expressed as weight percentages relative to the total weight of the composition.

TABLE 7

|  | 27 | 28 | 29 |
|---|---|---|---|
| Indigo [1] | 1 g | 1 g | 1 g |
| Glutaroin | 1 g | — | — |
| Dihydroxyacetone | — | 1 g | — |
| Benzoin | — | — | 1 g |
| Benzyl alcohol | 5 g | 5 g | 5 g |
| Ethanol | 15 g | 15 g | 15 g |
| Monoethanolamine | 2 g | 2 g | 2 g |
| Water | qs 100 g | qs 100 g | qs 100 g |

[1] Indigo, CAS = 482-89-3, sold by Sigma Aldrich

The compositions are prepared and applied to pairs of natural and permanent-waved locks of hair containing 90% white hairs, under the same conditions as in Example 6.

Powerful and fast blue colorations are obtained.

Example 8

The dye compositions according to the invention, the formulations of which are given in Table 8 below, are prepared. The amounts of the constituents are expressed as weight percentages relative to the total weight of the composition.

TABLE 8

|  | 30 | 31 | 32 |
|---|---|---|---|
| Indigo [1] | 0.5 g | 0.5 g | 0.5 g |
| Curcumin | 0.5 g | 0.5 g | 0.5 g |
| Isatin | 0.3 g | 0.3 g | 0.3 g |
| Orcein | 0.3 g | 0.3 g | 0.3 g |
| Chlorophylline | 0.15 g | 0.15 g | 0.15 g |
| Sorghum | 0.02 g | 0.02 g | 0.02 g |
| Lactic acid | 0.01 g | 0.01 g | 0.01 g |
| Acetoin | 1 g | 1 g | 1 g |
| Ethanol | 15 g | 15 g | 15 g |
| Benzyl alcohol | 5 g | 1 g | — |
| 3-Phenyl-1-propanol | — | 0.5 g | — |
| Decanol | — | — | 5 g |
| CTAB [6] | — | — | 2 g |
| Monoethanolamine | 2 g | 2 g | 2 g |
| Fragrance | qs | qs | qs |
| Water | qs 100 g | qs 100 g | qs 100 g |

[1] Indigo, CAS = 482-89-3, sold by Sigma Aldrich
[6] Cetyltrimethylammonium chloride The compositions are prepared and applied to pairs of natural and permanent-waved locks of hair containing 90% white hairs, under the same conditions as in Example 6.

Powerful and fast brown colorations are obtained.

Example 9

The dye compositions according to the invention, the formulations of which are given in Table 9 below, are prepared. Composition 33 is a comparative composition. Composition 34 is a composition according to the invention.

TABLE 9

|  | 33 | 34 |
|---|---|---|
| Indigo [1] | 1 g | 1 g |
| Benzyl alcohol | — | 5 g |
| Ethanol | 20 g | 15 g |
| Acetoin | 1 g | 1 g |
| Aqueous 10% sodium hydroxide solution | 12 g | 12 g |
| Aqueous 8% Polyquaternium-7 solution | 3 g | — |
| Water | qs 100 g | qs 100 g |

[1] Indigo, CAS = 482-89-3, sold by Sigma Aldrich

The compositions are left to stir under argon:
for 4 hours at 40° C. for solution 33
for 2 hours at 40° C. for solution 34.

It is noted that composition 33 is only partially dissolved, whereas composition 34 is fully dissolved.

The pH is then adjusted to 9.6 with 4 g of 25% aqueous ammonia solution and 4 g of aqueous 90% lactic acid solution.

The dissolution is markedly better in the case of composition 34 than in the case of composition 33.

Example 10

The dye compositions according to the invention, the formulations of which are given in Table 10 below, are prepared.

TABLE 10

|  | 35 | 36 | 37 | 38 |
|---|---|---|---|---|
| Isoindigo [2] | 1 g | 1 g | 1 g | 1 g |
| Shellfish red [3] | — | 1 g | — | — |
| Thioindigo [4] | — | — | 1 g | — |
| Oralith [5] | — | — | — | 1 g |
| Benzyl alcohol | 5 g | 5 g | 5 g | 5 g |
| Ethanol | 15 g | 15 g | 15 g | 15 g |
| Acetoin | 1 g | 1 g | 1 g | 1 g |
| Aqueous 10% sodium hydroxide solution | 12 g | 12 g | 12 g | 12 g |
| Water | qs 100 g | qs 100 g | qs 100 g | qs 100 g |

[2] Isoindigo
[3] Shellfish red, 6,6'-dibromoindigo sold by Kremer Pigmente
[4] Thioindigo, CAS = 522-75-8, sold by Sigma Aldrich
[5] Oralith, CAS = 2379-74-0, sold by Sigma Aldrich The compositions are left to stir under argon for 2 hours at 40° C.

The pH is then adjusted to 9.6 with 4 g of 25% aqueous ammonia solution and 4 g of aqueous 90% lactic acid solution.

Pairs of locks of natural and permanent-waved hair containing 90% white hair are dyed for 20 minutes at 40° C. with each of these dye compositions 35 to 38, and the locks are then drained, rinsed, shampooed and dried.

Powerful and fast colorations are obtained.

The dyeing results on the locks are observed visually and accompanied by colorimetric measurements are expressed as ΔE relative to undyed hair.

The colorimetric measurements may be taken using a Konica-Minolta CM-2600d spectrocolorimeter in the CIE L*a*b* system. In this system, L* represents the intensity of the coloration obtained; the lower the value of L*, the more intense the coloration obtained. The chromaticity is measured by the values a* and b*, a* indicating the value on the green/red color axis and b* indicating the value on the blue/yellow color axis.

The uptake is measured by ΔE using the formula:

$$\Delta E = \sqrt{(L^* - L_o^*)^2 + (a^* - a_o^*)^2 + (b^* - b_o^*)^2}$$

in which:
L*, a* and b* represent the parameters of the dyed hair and $L_o^*$, $a_o^*$ and $b_o^*$ represent the parameters of the undyed hair.

These colorimetric measurements are given in Table 11.

TABLE 11

|  | Uptake on natural hair | | | | Uptake on permanent-waved hair | | | |
|---|---|---|---|---|---|---|---|---|
|  | L* | a* | b* | ΔE/undyed hair | L* | a* | b* | ΔE/undyed hair |
| Undyed hair | 60.38 | 0.57 | 13.09 | — | 61.38 | 0.31 | 12.77 | — |
| Hair dyed with 34 | 34.46 | −4.06 | −6.04 | 32.55 | 25.58 | −0.3 | −8.31 | 41.55 |
| Hair dyed with 35 | 30.93 | −3.46 | −7.26 | 36.02 | 27.55 | −1.98 | −8.79 | 40.18 |
| Hair dyed with 36 | 46.24 | 7.64 | 0.9 | 19.96 | 39.64 | 11.18 | −4.48 | 29.81 |
| Hair dyed with 37 | 35.4 | 7.11 | −1.23 | 29.53 | 26.93 | 9.48 | −5.01 | 39.85 |
| Hair dyed with 38 | 44.68 | 19.35 | 2.94 | 26.49 | 34.99 | 24.99 | −0.12 | 39.36 |

Example 11

The dye compositions according to the invention, the formulations of which are given in Table 12 below, are prepared.

TABLE 12

|  | 39 | 40 | 41 |
|---|---|---|---|
| Indigo [1] | 1 g | 1 g | 1 g |
| Glutaroin | 1 g | — | — |
| Dihydroxyacetone | — | 1 g | — |
| Benzoin | — | — | 1 g |
| Benzyl alcohol | 5 g | 5 g | 5 g |
| Ethanol | 15 g | 15 g | 15 g |
| Aqueous 10% sodium hydroxide solution | 12 g | 12 g | 12 g |
| Water | qs 100 g | qs 100 g | qs 100 g |

[1] Indigo, CAS = 482-89-3, sold by Sigma Aldrich

The compositions are prepared and applied to pairs of natural and permanent-waved locks of hair containing 90% white hairs, under the same conditions as in Example 10.

Powerful and fast blue colorations are obtained.

Example 12

The dye compositions according to the invention, the formulations of which are given in Table 13 below, are prepared. Composition 42 is a comparative composition. Composition 43 is a composition according to the invention.

TABLE 13

|  | 42 | 43 |
|---|---|---|
| Diosindigo A | 1 g | 1 g |
| Benzyl alcohol | 5 g | 5 g |
| Ethanol | 15 g | 15 g |
| Acetoin | — | 1 g |
| Aqueous 10% sodium hydroxide solution | 12 g | 12 g |
| Water | qs 100 g | qs 100 g |

The compositions are left to stir under argon for 30 minutes at room temperature.

The pH of each composition is then adjusted to 9.6 with 4 g of 20% aqueous ammonia solution and 4 g of aqueous 90% lactic acid solution.

Pairs of locks of natural and permanent-waved hair containing 90% white hairs are then dyed using each of the compositions 42 and 43. The compositions are applied to the locks and, after a leave-on time of 30 minutes at room temperature, the locks are rinsed, shampooed and dried.

It is then found that little coloration is obtained on the locks of hair (natural and permanent-waved) dyed with composition 42, whereas a strong blue coloration is obtained for the locks of hair (natural and permanent-waved) dyed with composition 43.

The colorimetric measurements were taken using a Konica-Minolta CM-2600d spectrocolorimeter in the CIE L*a*b* system.

According to this system, L* represents the intensity of the coloration. The chromatic coordinates are expressed by the parameters a* and b*, a* corresponding to the red/green chromatic axis and b* to the yellow/blue chromatic axis.

The color uptake ΔE, which is the difference in color between the undyed locks and the dyed locks, is determined according to the following equation:

$$\Delta E = \sqrt{(L^* - L_o^*)^2 + (a^* - a_o^*)^2 + (b^* - b_o^*)^2}$$

In this equation, L*, a* and b* represent the values measured on the locks of dyed hair and $L_o^*$, $a_o^*$ and $b_o^*$ represent the values measured on the locks of undyed hair.

The larger the value of ΔE, the greater the difference in color between the dyed and undyed locks, which is representative of better uptake of the color onto the locks of hair.

The results obtained are as follows:

|  | 42 | 43 |
|---|---|---|
| Uptake on natural hair | 5.2 | 32.85 |
| Uptake on permanent-waved hair | 12.52 | 40.56 |

These results confirm that with composition 43 according to the invention, uptake of color onto the hair, both natural and permanent-waved, that is markedly superior to that of comparative composition 42 is obtained.

A lower value of the parameter L*, which reflects better intensity of the coloration, is also obtained with composition B according to the invention.

Example 13

The dye compositions according to the invention, the formulations of which are given in Table 14 below, are prepared.

TABLE 14

|  | 44 | 45 |
|---|---|---|
| 4,4'-diethoxy-2,2'-binaphthylidene-1,1'-dione | 1 g | — |
| 4,4'-bis(hexyloxy)-1H, 14H-2,2'-binaphthalene-1,1'-dione | — | 1 g |
| Benzyl alcohol | 5 g | 5 g |
| Ethanol | 15 g | 15 g |
| Acetoin | 1 g | 1 g |
| Aqueous 10% sodium hydroxide solution | 12 g | 12 g |
| Water | qs 100 g | qs 100 g |

The compositions are left to stir under argon at room temperature for:

3 hours 30 minutes for composition 44, 1 hour 30 minutes for composition 45.

The pH of each of the two compositions is then adjusted to 9.6 with 4 g of 20% aqueous ammonia solution and 4 g of aqueous 90% lactic acid solution.

Pairs of locks of natural and permanent-waved hair containing 90% white hairs are then dyed using each of the compositions 44 and 45. The compositions are applied to the locks and, after a leave-on time of 30 minutes at room temperature, the locks are rinsed, shampooed and dried.

It is then found that powerful, fast blue colorations are obtained with each of these two compositions.

Example 14

The dye compositions according to the invention, the formulations of which are given in Table 15 below, are prepared.

TABLE 15

|  | 46 | 47 | 48 |
|---|---|---|---|
| Diosindigo A | 1 g | 1 g | 1 g |
| Glutaroin | 1 g | — | — |
| Dihydroxyacetone | — | 1 g | — |

47

TABLE 15-continued

|  | 46 | 47 | 48 |
|---|---|---|---|
| Benzoin | — | — | 1 g |
| Benzyl alcohol | 5 g | 5 g | 5 g |
| Ethanol | 15 g | 15 g | 15 g |
| Aqueous 10% sodium hydroxide solution | 12 g | 12 g | 12 g |
| Water | qs 100 g | qs 100 g | qs 100 g |

The compositions are left to stir under argon at room temperature until dissolution of the ingredients is complete.

The pH of each of the three compositions is then adjusted to 9.6 with 4 g of 20% aqueous ammonia solution and 4 g of aqueous 90% lactic acid solution.

Pairs of locks of natural and permanent-waved hair containing 90% white hairs are then dyed using each of the compositions 46, 47 and 48. The compositions are applied to the locks and, after a leave-on time of 30 minutes at room temperature, the locks are rinsed, shampooed and dried.

It is then found that powerful, fast blue colorations are obtained with each of these three compositions.

Example 15

The dye compositions according to the invention, the formulations of which are given in Table 16 below, are prepared.

TABLE 16

|  | 49 | 50 | 51 |
|---|---|---|---|
| Diosindigo A | 0.5 g | 0.5 g | 0.5 g |
| Curcumin | 0.5 g | 0.5 g | 0.5 g |
| Isatin | 0.3 g | 0.3 g | 0.3 g |
| Orcein | 0.3 g | 0.3 g | 0.3 g |
| Chlorophylline | 0.15 g | 0.15 g | 0.15 g |
| Sorghum | 0.02 g | 0.02 g | 0.02 g |
| Lactic acid | 0.01 g | 0.01 g | 0.01 g |
| Acetoin | 1 g | 1 g | 1 g |
| Ethanol | 15 g | 15 g | 15 g |
| Benzyl alcohol | 5 g | 1 g | — |
| 3-Phenyl-1-propanol | — | 0.5 g | — |
| Decanol | — | — | 5 g |
| Cetyltrimethylammonium chloride | — | — | 2 g |
| Aqueous 10% sodium hydroxide solution | 12 g | 12 g | 12 g |
| Fragrance | qs | qs | qs |
| Water | qs 100 | qs 100 | qs 100 |

The compositions are left to stir under argon at room temperature until dissolution of the ingredients is complete.

The pH of each of the three compositions is then adjusted to 9.6 with 4 g of 20% aqueous ammonia solution and 4 g of aqueous 90% lactic acid solution.

Pairs of locks of natural and permanent-waved hair containing 90% white hairs are then dyed using each of the compositions 49, 50 and 51. The compositions are applied to the locks and, after a leave-on time of 30 minutes at room temperature, the locks are rinsed, shampooed and dried.

It is then found that powerful, fast, natural colorations are obtained with each of these three compositions.

What is claimed is:

1. A dye composition comprising:
    one or more hydrophobic direct dyes with a logP of greater than or equal to 2 chosen from indigoid dyes and compounds of formulae (III) and (IV) below:

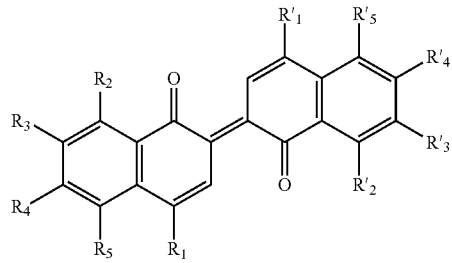

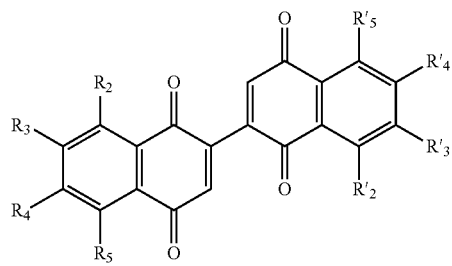

in which:
    $R_1$, $R'_1$, $R_2$, $R'_2$, $R_3$, $R'_3$, $R_4$, $R'_4$, $R_5$ and $R'_5$, which may be identical or different, represent a hydrogen atom, a halogen atom, a hydroxyl radical, a $C_1$ to $C_{30}$ alkyl, $C_1$ to $C_{30}$ alkyloxy, $C_1$ to $C_{30}$ acyl or $C_1$ to $C_{30}$ acyloxy radical, the alkyl and alkyloxy radicals possibly being substituted with one or more halogen atoms and/or with one or more hydroxyl groups,
    one or more organic alkaline agents, and/or one or more mineral bases chosen from carbonates, hydrogen carbonates, sodium hydroxide and potassium hydroxide, and mixtures thereof,
    one or more compounds (I) comprising in their structure a sequence:

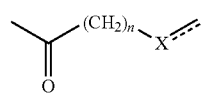

with n denoting an integer ranging from 0 to 4, and

denoting a group:

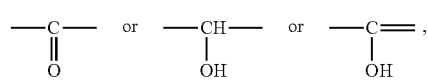

and
    one or more organic compounds (II) with a Hansen solubility parameter δH of less than or equal to 16 $MPa^{1/2}$ and with a molecular weight of less than 250 g/mol.

2. The composition as claimed in claim 1, wherein, in formulae (III) and (IV):
    the radicals $R_1$ and $R'_1$, which may be identical or different, represent a hydrogen atom, a $C_1$ to $C_{10}$ alkyl radical or a $C_1$ to $C_{10}$ alkyloxy radical, these radicals possibly being substituted with one or more halogen atoms and/or with one or more hydroxyl groups, and/or the radicals $R_2$, $R'_2$, $R_3$, $R'_3$, $R_4$, $R'_4$, $R_5$ and $R'_5$, which may be identical or different, represent a hydrogen atom, a halogen atom, a hydroxyl radical or a $C_1$ to $C_{10}$ alkyl or alkyloxy radical, these radicals possibly being substituted with one or more halogen atoms and/or with one or more hydroxyl groups.

3. The composition as claimed in claim 1, wherein:

the indigoid dyes are chosen from indigo, isoindigo, indirubin, isoindirubin, 4,4'dibromoindigo, 6,6'-dibromoindigo, 5,5'-dibromoindigo, cis-6,6'-dibromoindigo, 5,5',7,7'-tetrabromoindigo, 4,4',7,7'-tetrachloroindigo, 3H-indol-3-one, 1,2-dihydro-2-(3-oxobenzo[b]thien-2-(3H)-ylidene), thioindigo, Vat Red 1, cis-thioindigo, 6,6'-dichloro-4,4'-dimethylindigo, 5,5'-dichloro-7,7'-dimethylindigo, 4,4'-7,7'-tetramethylindigo, thioindigo Scarlet R, 2H-indol-2-one, 1,3-dihydro-3-(3-oxobenzo[b]thien-2(3H)-ylidene)-, (3E)-, thioindirubin, 2H-indol-2-one, 1,3-dihydro-3-(2-oxobenzo[b]thiophen-3(2H)-ylidene), benzo[b]thiophen-2(3H)-one and 3-(2-oxobenzo[b]thiophen-3(2H)-ylidene, the compounds of formulae (III) and (IV) are chosen from Indigo Russig's Blue, Diosindigo A, Diosindigo B, 4,4'-diethoxy-2,2'-binaphthylidene-1,1'-dione, 4,4'bis(hexyloxy)-1H,14H-2,2'-binaphthalene-1,1'-dione, mamegakinone and biramentaceone.

4. The composition as claimed in claim 1, wherein the hydrophobic direct dye(s) represent from 0.001% to 20% by weight relative to the total weight of the cosmetic composition.

5. The composition as claimed in claim 1, wherein the compound(s) (I) have in their structure a sequence:

$$-\underset{\underset{O}{\parallel}}{C}-\underset{\underset{OH}{|}}{CH}- \quad (A)$$

or $$-\underset{\underset{OH}{|}}{C}=\underset{\underset{OH}{|}}{C}- . \quad (B)$$

6. The composition as claimed in claim 1, wherein the compound(s) (I) correspond to formula (C) below:

$$R_1-\underset{\underset{O}{\parallel}}{C}-(CH_2)_n-X\diagdown Y \quad (C)$$

with:

n denoting an integer from 0 to 4, and $-X\!\!=\!\!\!=\!Y$ denoting a group $$-\underset{\underset{O}{\parallel}}{C}-R_2 \quad \text{or} \quad -\underset{\underset{OH}{|}}{CH}-R_2 \quad \text{or} \quad -\underset{\underset{OH}{|}}{C}=CHR_2,$$

$R_1$ and $R_2$ representing, independently of each other, a hydrogen atom; a substituted or unsubstituted phenyl radical; a hydroxyl radical; a $C_1$-$C_4$ alkoxy radical; a linear or branched $C_1$-$C_4$ alkyl radical, which is unsubstituted or substituted with one or two radicals chosen from the radicals —OR', —C(O)R" and —COOR''', with R', R" and R''' representing, independently of each other, a hydrogen atom or a linear or branched $C_1$-$C_4$ alkyl radical, or $R_1$ and $R_2$ forming, with the carbon-based chain to which they are attached, an unsubstituted 5- or 6-membered nonaromatic carbon-based ring.

7. The composition as claimed claim 1, wherein the compound(s) (I) represent from 0.01% to 20% by weight relative to the total weight of the cosmetic composition.

8. The composition as claimed in claim 1, wherein the organic alkaline agent(s) have a pKb at 25° C. ranging from 1 to 12, the mineral base(s) are chosen from alkali metal carbonates and alkali metal hydrogen carbonates and mixtures thereof, preferably from sodium carbonate, potassium carbonate, sodium hydrogen carbonate and potassium hydrogen carbonate, and mixtures thereof.

9. The composition as claimed in claim 1, wherein the organic alkaline agent(s) are organic amines selected from the group consisting of:

(1) amines comprising a primary, secondary or tertiary amine function, and one or more linear or branched C1-C8 alkyl groups bearing one or more hydroxyl radicals, (2) organic amines of the following formula:

$$\underset{Ry}{\overset{Rx}{\diagdown}}N-W-N\underset{Rt}{\overset{Rz}{\diagup}}$$

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ amino alkyl radical, (3) amino acids, (4) organic amines of heterocyclic type, (5) amino acid dipeptides, and (6) compounds comprising a guanidine function.

10. The composition as claimed in claim 1, wherein the organic alkaline agent(s) and/or the mineral base(s) represent from 0.1% to 20% by weight relative to the total weight of the composition.

11. The composition as claimed in claim 1, wherein the organic compound(s) (II) have a Hansen solubility parameter δH of less than 16, these compound(s) being present in a content ranging from 0.1% to 20% by weight relative to the total weight of the composition.

12. The composition as claimed in claim 1, wherein the organic compound(s) (II) are chosen from alkanols, aliphatic esters, ethers, aromatic alcohols, alkylaryl alcohols, aromatic acids, aliphatic acids, alkylene carbonates, and lactones, and mixtures thereof.

13. The composition as claimed in claim 1, further comprising:

one or more additional dyes, other than dyes of hydrophobic nature with a logP of greater than or equal to 2, chosen from natural dyes and nonnatural direct dyes, oxidation dye precursors, and combinations thereof, and/or one or more oxidizing agents.

14. A dyeing process that comprises applying to keratin fibers, a composition as defined in claim 1.

* * * * *